(12) United States Patent
Priebe et al.

(10) Patent No.: US 7,109,177 B2
(45) Date of Patent: *Sep. 19, 2006

(54) METHODS AND COMPOSITIONS FOR THE MANUFACTURE OF C-3' AND C-4' ANTHRACYCLINE ANTIBIOTICS

(75) Inventors: Waldeman Priebe, Houston, TX (US); Izabella Fokt, The Woodlands, TX (US); Teresa Przewloka, Burlington, MA (US); Marta Krawczyk, Greenfield, WI (US); Piotr Skibicki, Warsaw (PL); Grzegorz Grynkiewicz, Lominaki (PL); Roman Perez-Soler, New York, NY (US)

(73) Assignee: Houston Pharmaceuticals, Inc., Houston, TX (US)

( * ) Notice: Subject to any disclaimer, the term of this patent is extended or adjusted under 35 U.S.C. 154(b) by 148 days.

This patent is subject to a terminal disclaimer.

(21) Appl. No.: 10/752,426

(22) Filed: Jan. 6, 2004

(65) Prior Publication Data

US 2005/0004048 A1    Jan. 6, 2005

Related U.S. Application Data

(63) Continuation of application No. 09/956,588, filed on Sep. 19, 2001, now Pat. No. 6,673,907, which is a continuation of application No. PCT/IB00/00527, filed on Mar. 15, 2000.

(60) Provisional application No. 60/125,505, filed on Mar. 19, 1999.

(51) Int. Cl.
*A61K 31/70*  (2006.01)
*C07H 15/24*  (2006.01)

(52) U.S. Cl. .......................................... 514/34; 536/6.4
(58) Field of Classification Search ................ 536/6.4; 514/34
See application file for complete search history.

(56) References Cited

U.S. PATENT DOCUMENTS

| 4,355,026 A | 10/1982 | Umezawa et al. ............ 514/34 |
| 5,319,077 A | 6/1994  | Kinzy ....................... 536/17.2 |
| 5,625,043 A | 4/1997  | Priebe et al. ................ 536/6.4 |

OTHER PUBLICATIONS

International Search Report dated Oct. 5, 2000.

*Primary Examiner*—Elli Peselev
(74) *Attorney, Agent, or Firm*—Fulbright & Jaworski L.L.P.

(57) ABSTRACT

The present invention discloses new and novel substituted anthracyclines with modified alkyl-aromatic ring substitutions on the C-3' of the sugar moiety or modified or unmodified alkyl-aromatic ring substitutions at the C-4' of the sugar moiety. It also discloses novel methods for the preparation of sugar substrates and methods for the preparation of anthracycline antibiotics. These anthracycline analogs show high cytotoxicity in vitro against several tumor cell lines.

13 Claims, 22 Drawing Sheets

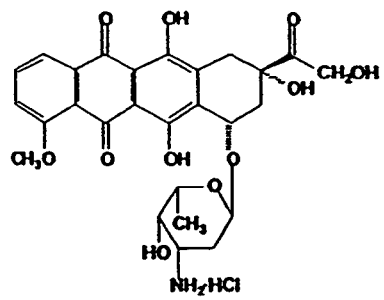
DOXORUBICIN
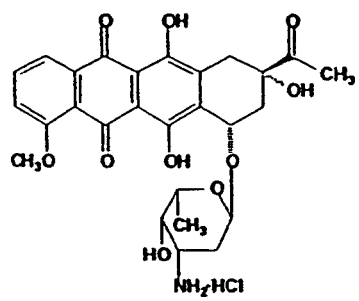
DAUNORUBICIN
FIG. 1. Structure of Doxorubicin and Daunorubicin
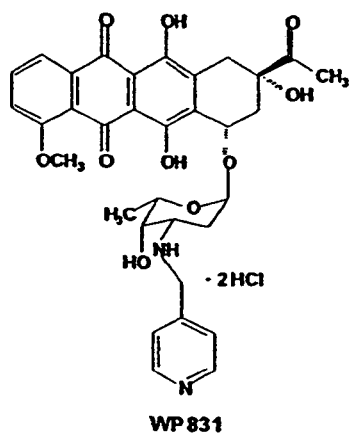
FIG. 2 Structure of WP831

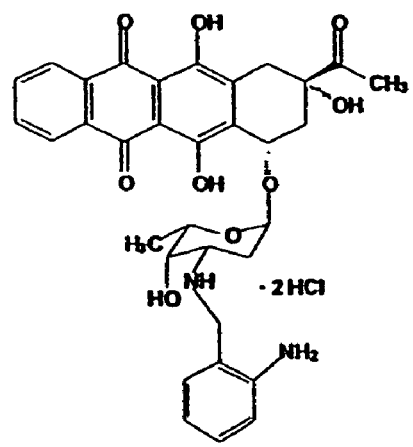
FIG. 3 Structure of WP791
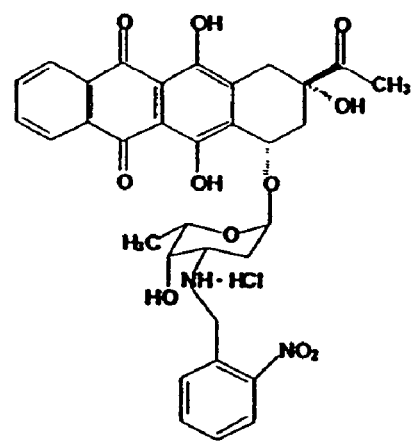
FIG. 4 Structure of WP790

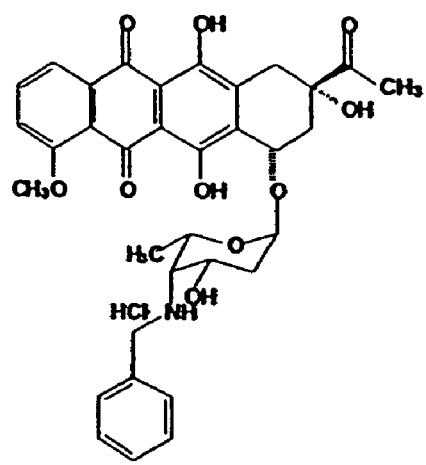
FIG. 5  Structure of WP787
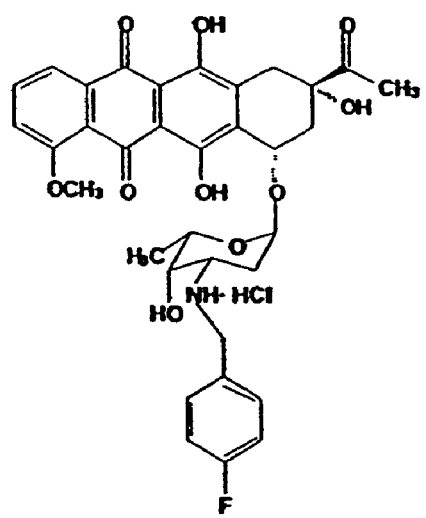
FIG. 6  Stucture of WP786

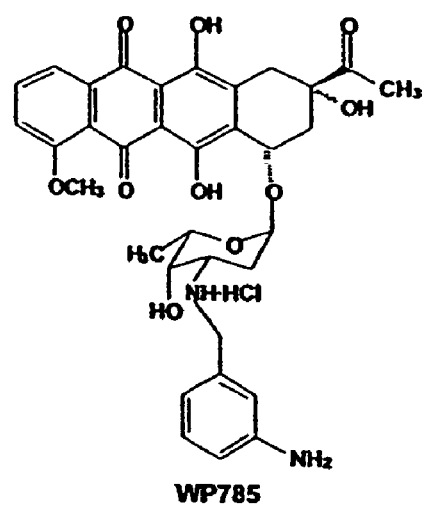
FIG. 7 Stucture of WP785
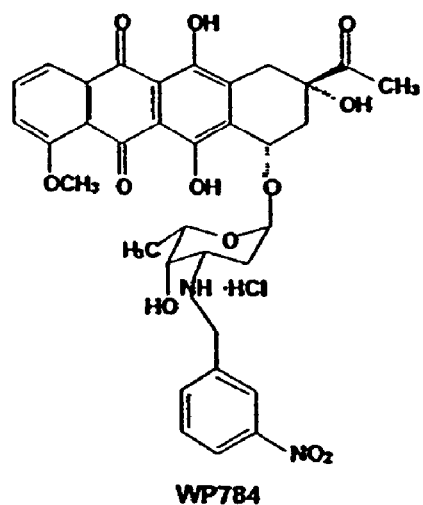
FIG. 8 Structure of WP784

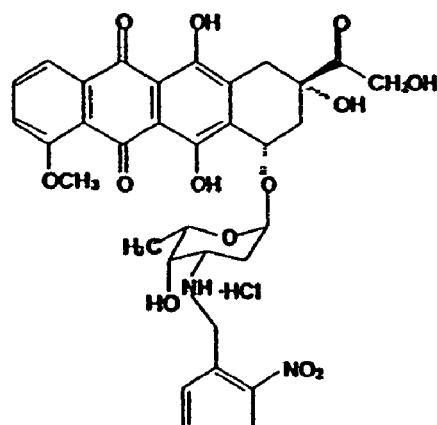
FIG. 9 Structure of WP780
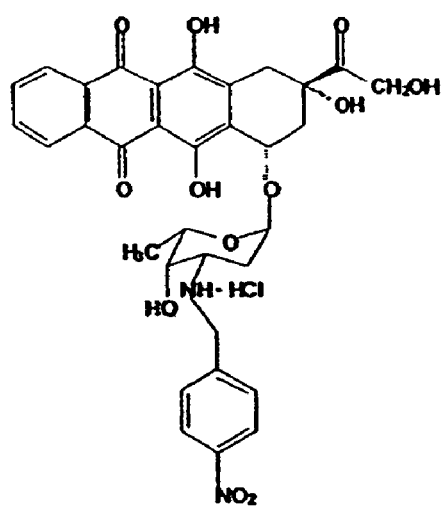
FIG. 10 Stucture of WP778

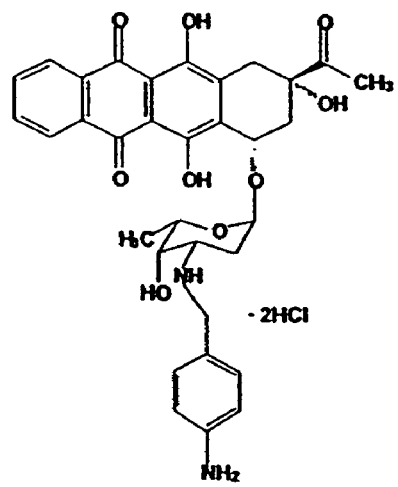
FIG. 11 Structure of WP775
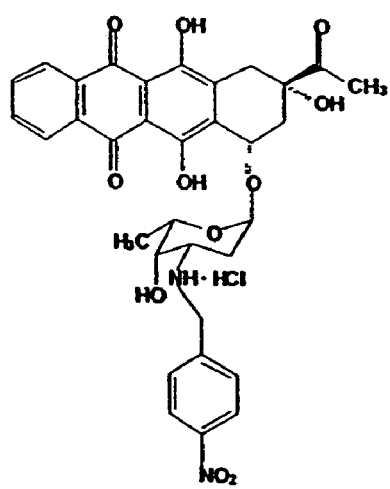
FIG. 12 Structure of WP774

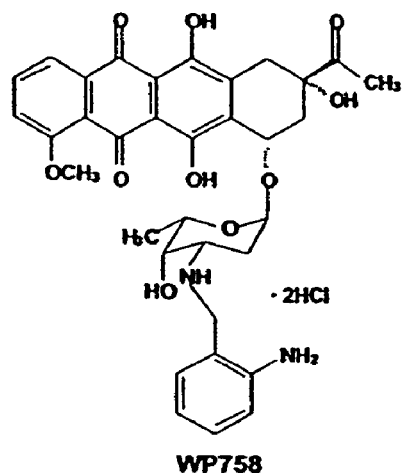
FIG. 13 Structure of WP758
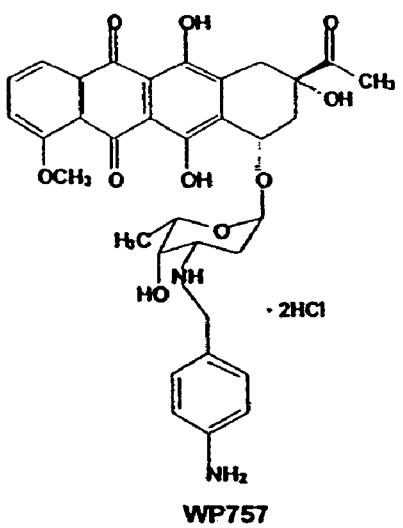
FIG. 14 Structure of WP757

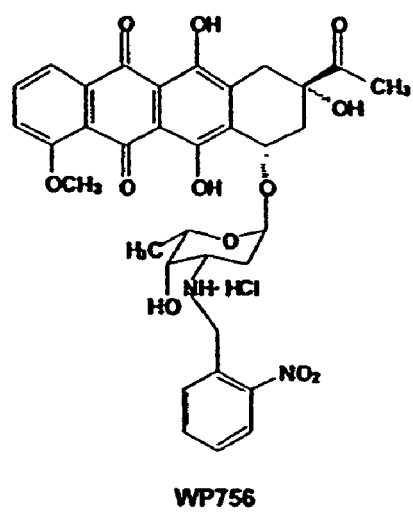
FIG. 15 Structure WP756
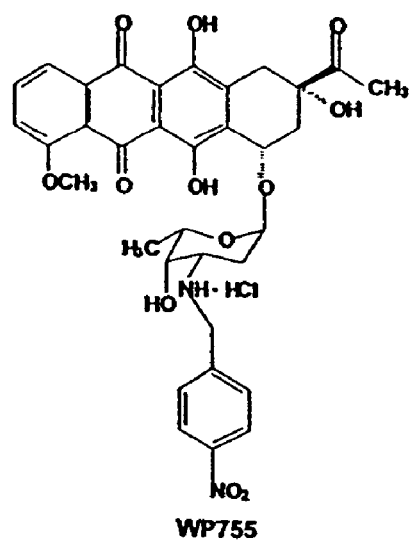
FIG. 16 Structure WP755

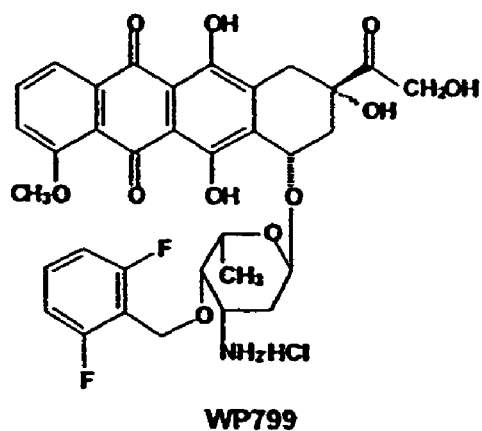
FIG. 17 Structure of WP799
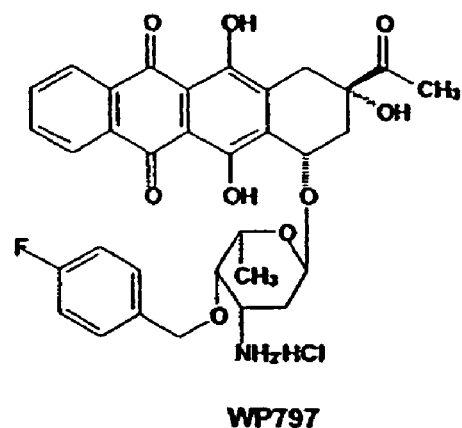
FIG. 18 Structure of WP797

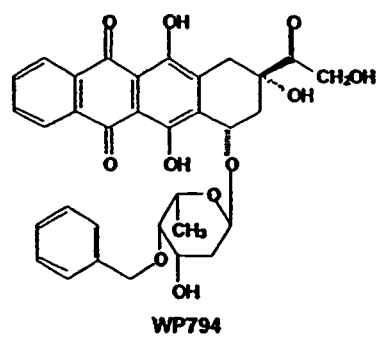
FIG. 19 Structure of WP794
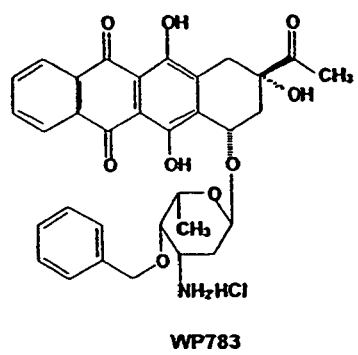
FIG. 20 Structure of WP783
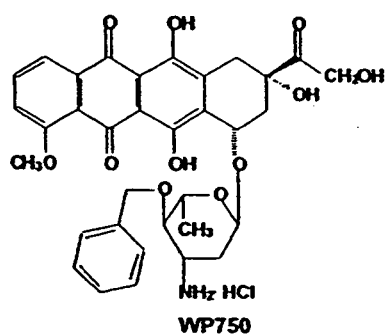
FIG. 21 Structure of WP750

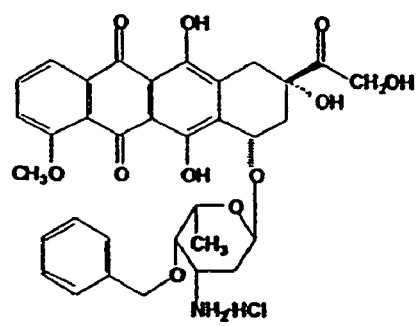
FIG. 22 Structure of WP744
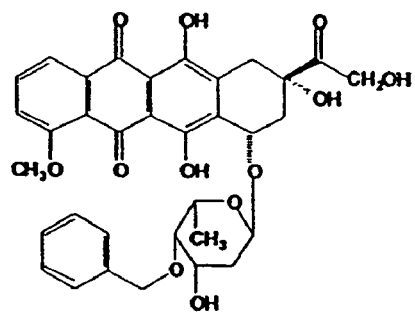
FIG. 23 Structure of WP727
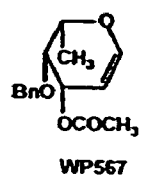
FIG. 24 Structure of WP567

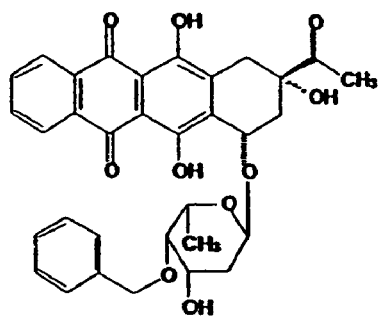
FIG. 25 Structure of WP793
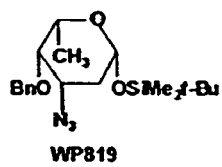
FIG. 26 Structure of WP819
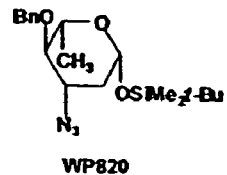
FIG. 27 Structure of WP820

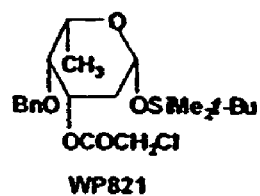
FIG. 28 WP821
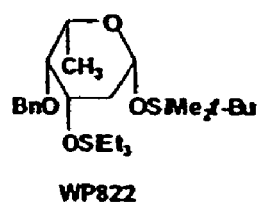
FIG. 29 Structure of WP822
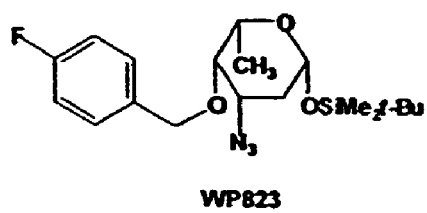
FIG. 30 Structure of WP823

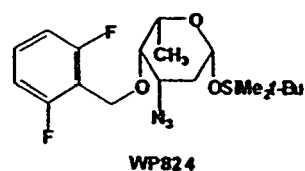
FIG. 31 Structure of WP824
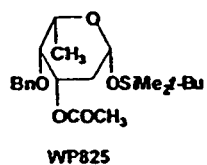
FIG. 32 Structure of WP825
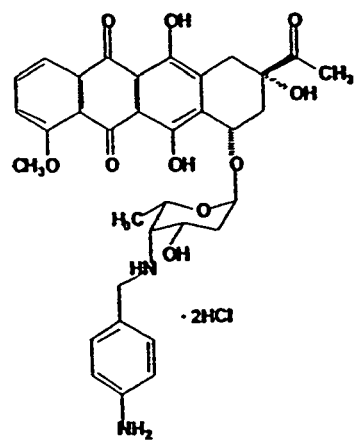
FIG. 33 Structure of WP764

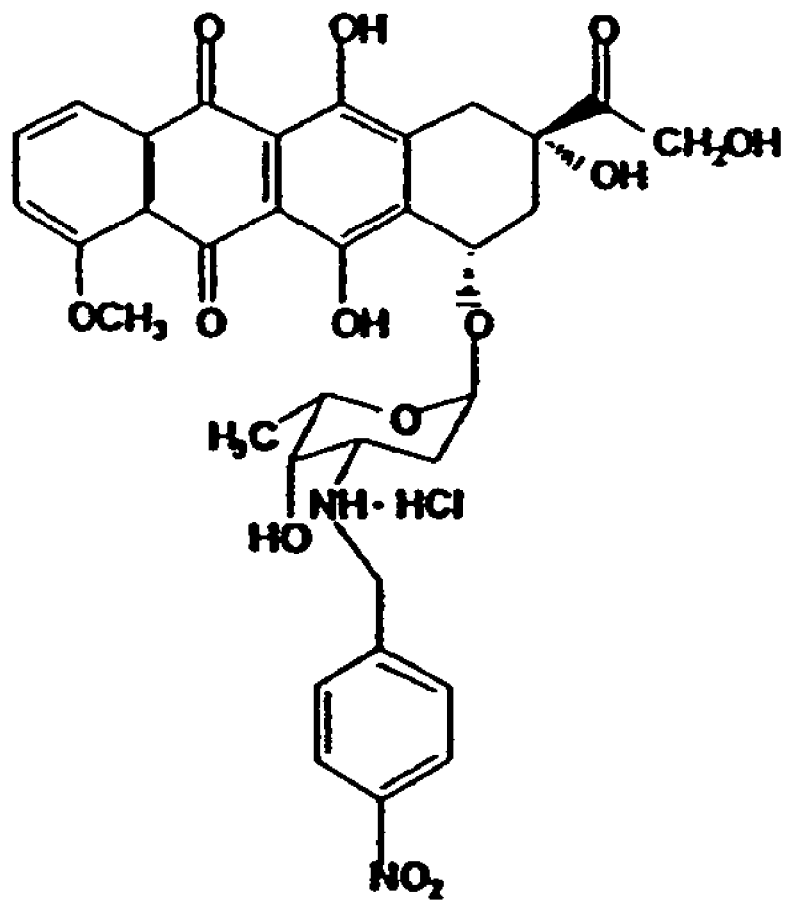
FIG. 34 Structure of WP765

FIG. 39

Examples of Selective Alkylation of Acylated Glycals

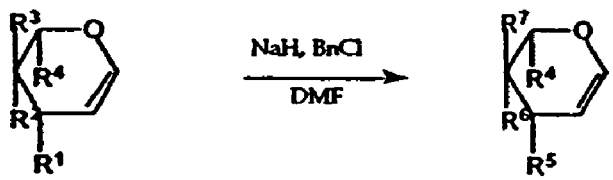

L-Rhamnal: WP- $R^1$=OAc, $R^2$=H, $R^3$=OAc, $R^4$=Me, $R^5$=OH, $R^6$=H, $R^7$=OBn
L-Rhamnal: WP- $R^1$=OAc, $R^2$=H, $R^3$=OAc, $R^4$=Me, $R^5$=OAc, $R^6$=H, $R^7$=OBn
L-Fucal: WP- $R^1$=OAc, $R^2$=OAc, $R^3$=H, $R^4$=Me, $R^5$=OH, $R^6$=OBn, $R^7$=H
L-Fucal: WP- $R^1$=OAc, $R^2$=OAc, $R^3$=H, $R^4$=Me, $R^5$=OAc, $R^6$=OBn, $R^7$=H
L-Xylal: WP- $R^1$=OAc, $R^2$=H, $R^3$=OAc, $R^4$=H, $R^5$=OAc, $R^6$=H, $R^7$=OBn

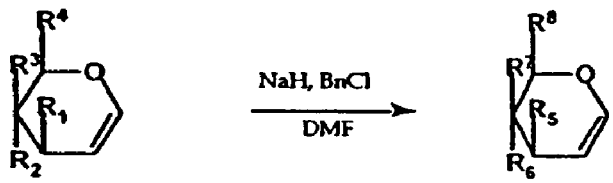

D-Glucal: WP- $R^1$=OAc, $R^2$=OAc, $R^3$=H, $R^4$=CH$_2$OAc, $R^5$=OH, $R^6$=OBn, $R^7$=H, $R^8$=CH$_2$OH
D-Glucal: WP- $R^1$=OAc, $R^2$=OAc, $R^3$=H, $R^4$=CH$_2$OAC, $R^5$=OAc, $R^6$=OBn, $R^7$=H, $R^8$=CH$_2$OAc
D-Galactal: WP- $R^1$=OAc, $R^2$=H, $R^3$=OAc, $R^4$=CH$_2$OAc, $R^5$=OH, $R^6$=H, $R^7$=OBn, $R^8$=CH$_2$OH
D-Galactal: WP- $R^1$=OAc, $R^2$=H, $R^3$=OAc, $R^4$=CH$_2$OAc, $R^5$=Ac, $R^6$=H, $R^7$=OBn, $R^8$=CH$_2$OA
D-Arabinal: WP- $R^1$=OAc, $R^2$=H, $R^3$=OAc, $R^4$=H, $R^5$=OH, $R^6$=H, $R^7$=OH, $R^8$=H Synthesis of 3'-azido-sugars and its 4-O-benzylated derivatives

FIG. 41
ALTERNATIVE SYNTHESIS OF 3-AZIDO-4-O-BENZYL-DAUNOSAMINE FROM 3-AZIDOACOSAMINE
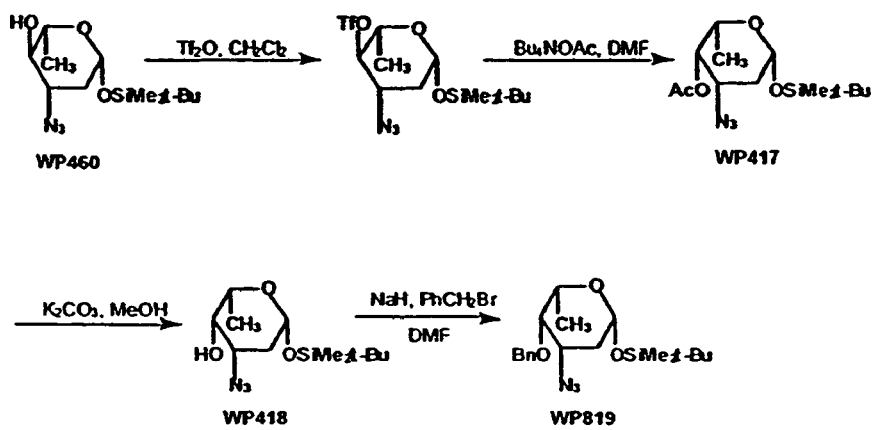
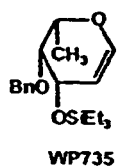
FIG. 42 Structure of WP735
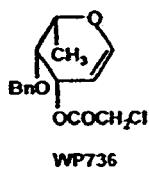
FIG. 43 Structure of WP736

METHODS AND COMPOSITIONS FOR THE MANUFACTURE OF C-3' AND C-4' ANTHRACYCLINE ANTIBIOTICS

This application is a continuation of U.S. application Ser No. 09/956,588, filed Sep. 19, 2001, now U.S. Pat. No. 6,673,907, which issued on Jan. 6, 2004, which is a continuation of International Application No. PCT/IB00/00527 filed Mar. 15, 2000, which claims the benefit of U.S. Provisional Application No. 60/125,505, filed Mar. 19, 1999. The entire text of these applications are specifically incorporated into this specification by reference.

The U.S. Government may owns rights in the present invention pursuant to National Institute of Health grants numbered C3A55270 and CA50320.

BACKGROUND OF THE INVENTION

1. Field of the Invention

The present invention relates generally to the treatment of cancer. More particularly, it concerns novel compounds useful for chemotherapy, methods of synthesis of these compounds and methods of treatment employing these compounds. These novel drugs comprise two main classes of compounds; one bearing modified substituents at the C-3' sugar moiety and the other bearing modifications at the C4' sugar moiety. In addition, some of these analogs might also be modified at the aglycon and/or sugar moiety. These novel anthracycline analogs display high anti-tumor activity and can be used as potent drugs active against multi-drug resistant tumors. These compounds are related to other anti-tumor anthracyclines such as daunorubicin, idarubicin, epirubicin, and doxorubicin. The cytotoxic potency of these new compounds is significantly higher when compared to doxorubicin.

2. Description of Related Art

Resistance of tumor cells to the killing effects of chemotherapy is one of the central problems in the management of cancer. It is now apparent that at diagnosis many human tumors already contain cancer cells that are resistant to standard chemotherapeutic agents. Spontaneous mutation toward drug resistance is estimated to occur in one of every $10^6$ to $10^7$ cancer cells. This mutation rate appears to be independent of any selective pressure from drug therapy, although radiation therapy and chemotherapy may give rise to additional mutations and contribute to tumor progression within cancer cell populations (Goldie et al., 1979; Goldie et al., 1984; Nowell, 1986). The cancer cell burden at diagnosis is therefore of paramount importance because even tumors as small as 1 cm ($10^9$ cells) could contain as many as 100 to 1,000 drug-resistant cells prior to the start of therapy.

Selective killing of only the tumor cells sensitive to the drugs leads to an overgrowth of tumor cells that are resistant to the chemotherapy. Mechanisms of drug resistance include decreased drug accumulation (particularly in multi-drug resistance), accelerated metabolism of the drug and other alterations of drug metabolism, and an increase in the ability of the cell to repair drug-induced damage (Curt et al., 1984; and Kolate, 1986). The cells that overgrow the tumor population not only are resistant to the agents used but also tend to be resistant to other drugs, many of which have dissimilar mechanisms of action. This phenomenon, called pleiotropic drug resistance or multi-drug resistance (MDR), may account for much of the drug resistance that occurs in previously treated cancer patients. The development of drug resistance is one of the major obstacles in the management of cancer. One of the traditional ways to attempt to circumvent this problem of drug resistance has been combination chemotherapy.

Combination drug therapy is the basis for most chemotherapy employed to treat breast, lung, and ovarian cancers as well as Hodgkin's disease, non-Hodgkin's lymphomas, acute leukemias, and carcinoma of the testes. Combination chemotherapy uses the differing mechanisms of action and cytotoxic potentials of multiple drugs.

Although combination chemotherapy has been successful in many cases, the need still exists for new anti-cancer drugs. These new drugs could be such that they are useful in conjunction with standard combination chemotherapy, or these new drugs could attack drug resistant tumors by having the ability to kill cells of multiple resistance phenotypes.

A drug that exhibits the ability to overcome multiple drug resistance could be employed as a chemotherapeutic agent either alone or in combination with other drugs. The potential advantages of using such a drug in combination with chemotherapy would be the need to employ fewer toxic compounds in the combination, cost savings, and a synergistic effect leading to a treatment regime involving fewer treatments.

The commonly used chemotherapeutic agents are classified by their mode of action, origin, or structure,although some drugs do not fit clearly into any single group. The categories include alkylating agents, anti-metabolites, antibiotics, alkaloids, and miscellaneous agents (including hormones). Agents in the different categories have different sites of action.

Antibiotics are biologic products of bacteria or fungi. They do not share a single mechanism of action. The anthracyclines daunorubicin and doxorubicin (DOX) are some of the more commonly used chemotherapeutic antibiotics. The anthracyclines achieve their cytotoxic effect by several mechanisms, including inhibition of topoisomerase II; intercalation between DNA strands, thereby interfering with DNA and RNA synthesis; production of free radicals that react with and damage intracellular proteins and nucleic acids; chelation of divalent cations; and reaction with cell membranes. The wide range of potential sites of action may account for the broad efficacy as well as the toxicity of the anthracyclines (Young et al., 1985).

The anthracycline antibiotics are produced by the fungus *Streptomyces peuceilius* var. *caesius*. Although they differ only slightly in chemical structure, daunorubicin has been used primarily in the acute leukemias, whereas doxorubicin displays broader activity against human neoplasms, including a variety of solid tumors. The clinical value of both agents is limited by an unusual cardiomyopathy, the occurrence of which is related to the total dose of the drug; it is often irreversible. In a search for agents with high anti-tumor activity but reduced cardiac toxicity, anthracycline derivatives and related compounds have been prepared. Several of these have shown promise in the early stages of clinical study, and some, like epirubicin and idarubicin, are used as drugs. Epirubicin outsells doxorubicin in Europe and Japan, but it is not sold in the U.S.

The anthracycline antibiotics have tetracycline ring structures with an unusual sugar, daunosamine, attached by glycosidic linkage. Cytotoxic agents of this class all have quinone and hydroquinone moieties on adjacent rings that permit them to function as electron-accepting and donating agents. Although there are marked differences in the clinical use of daunorubicin and doxorubicin, their chemical structures differ only by a single hydroxyl group on C14. The chemical structures of daunorubicin and doxorubicin are shown in FIG. 1.

Doxorubicin's broad spectrum of activity against most hematological malignancies as well as carcinomas of the lung, breast, and ovary has made it a leading agent in the treatment of neoplastic disease (Arcamone,1981; Lown, 1988; Priebe, 1995). Since the discovery of daunorubicin and doxorubicin (FIG. 1), the mechanistic details of the anti-tumor activity of anthracycline antibiotics have been actively investigated (Priebe, 1995a; Priebe, 1995b; Booser, 1994).

Unfortunately, concomitant with its anti-tumor activity, DOX can produce adverse systemic effects, including acute myelosuppression, cumulative cardiotoxicity, and gastrointestinal toxicity (Young et al., 1985). At the cellular level, in both cultured mammalian cells and primary tumor cells, DOX can select for multiple mechanisms of drug resistance that decrease its chemotherapeutic efficacy. These mechanisms include P-gp-mediated MDR and MPR-rediated MDR, characterized by the energy-dependent transport of drugs from the cell (Bradley et al., 1988), and resistance conferred by decreased topoisomerase II activity, resulting in the decreased anthracycline-induced DNA strand scission (Danks et al., 1987; Pommier et al., 1986; Moscow et al., 1988).

Among the potential avenues of circumvention of systemic toxicity and cellular drug resistance of the natural anthracyclines is the development of semi-synthetic anthracycline analogues which demonstrate greater tumor-specific toxicity and less susceptibility to various forms of resistance.

SUMMARY OF THE INVENTION

The present invention seeks to overcome drawbacks inherent in the prior art by providing compositions of agents that display increased cytotoxicity when compared with doxorubicin and can prevent and/or overcome multi-drug resistance and exhibit reduced cardiotoxicity. This invention involves novel compounds that have utility as anti-tumor and/or chemotherapeutic drugs, methods of synthesizing these compounds and methods of using these compounds to treat patients with cancer. The invention is based on the discovery that anthracycline derivatives with substitutions attached to their C-3' or C-4' carbons in the sugar moiety have a surprisingly strong ability to kill multi-drug resistant tumor cells.

New anthracycline-based agents designed to interact and crosslink with DNA have been synthesized. These analogs contain substitutions at the C-3' or C4' sugar moiety. Synthesized compounds displayed activity significantly higher than that of parental daunorubicin or doxorubicin. In brief, in vitro the compounds WP755, WP756, WP757, WP758, WP775, WP778, WP784, WP786, WP790, WP791 modified at the C-3' and WP744, WP783 and WP750 modified at the C-4' were significantly more effective as measured by resistance index (RI) (Table 2). The RI values for the 3'-O-substituted analogs vary from 1.2 to 36 and are low when compared to the RI value of 253 and >200 for DOX, wherein, a higher RI value indicates that a compound is less effective against MDR. Similarly, RI values were very low (1.4-D8.8) for 4'-O-alkylated analogs whereas RI values for DOX varied from >42.6 to >200 for MDR1 type of resistance and from 10 to 16 for the MRP form of resistance. Lower RI values indicate greater efficacy of the drug against MDR tumors. The inventors also designed and synthesized other analogs. The observed activity and high potency against multi-drug resistant tumors indicate that these analogs are different from the parental drugs like doxorubicin and daunorubicin.

The inventors synthesized a series of analogs substituted at the aromatic ring of the C-3'-substituent which were then combined with modifications at the aglycon moiety. The inventors discovered that substitution at the aromatic ring increased the potency and alter the mechanism of action of the drugs making them significantly more active than doxorubicin. The mechanism of action of this class of drugs might involve direct interaction of the aromatic ring with cellular targets like DNA, topoisomerase II and topoisomerase I. Substitution of a benzyl ring at C-3' modifies drug interaction with P-glycoprotein, and subsequently the resistance index, thereby makes these compounds more effective against MDR tumors in comparison to the parent drug. In vitro evaluation identified the following C-3' substituted anthracycline analogs: WP831, WP791, WP790, WP786, WP785, WP784, WP780, WP778, WP775, WP774, WP765, WP758, WP757, WP756 and WP755 as unusually effective cytotoxic agents when compared to DOX.

The inventors also synthesized anthracycline analogs with substitutions at the C-4' sugar and demonstrated that these analogs overcome both, (a) multi-drug resistance (MDR) caused by overexpression of the MDR1 gene and (b) MDR-associated protein (MRP)-related resistance caused by overexpression of the MRP gene. Such modifications also contribute to the drugs ability to circumvent others forms of drug resistance and increased bioavailability. An increased steric hindrance at C-4' in doxorubicin might reduce drug interaction with P-glycoprotein and MRP and in combination, the increased lipophilicity caused by introduction of aromatic ring further contributes to increase intracellular drug concentration in MDR cells. Such modifications alter cellular uptake and retention of the drugs without affecting interaction with cellular targets, which results in cytotoxic effects. In vitro evaluation identified the following C-4' substituted anthracycline analogs: WP799, WP797, WP794, WP787, WP783, WP750, WP744, WP727, WP764 and WP571 as unusually potent cytotoxic agents when compared to DOX.

The anthracycline compounds bearing the C-3' substitutions have among others, O-Benzyl, N-Benzyl or S-Benzyl substitutions where the phenyl, an aromatic ring of the benzyl group is substituted. The compounds bearing C-4' substitutions at the sugar have among others, O-Benzyl, N-Benzyl or S-Benzyl substitutions where the benzyl group is a substituted or an unsubstituted benzene group. These compounds are depicted in FIGS. 2–25. These compounds exhibit cytotoxic activity substantially different from the activities of doxorubicin or daunorubicin. These compounds are active against doxorubicin resistant tumors and/or are usually similar or more cytotoxic than doxorubicin against sensitive tumors.

In some specific embodiments, the C-3'-substituted anthracycline compounds of the present invention have the general formula:

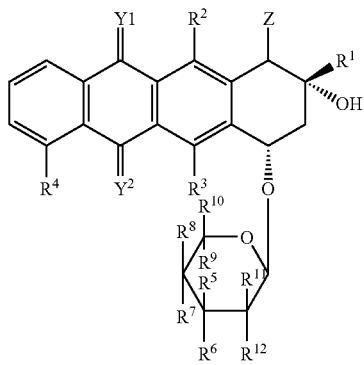

wherein, $R^1$ denotes any suitable group or combination of groups that form but are not limited to a nucleic acid intercalator or binding compound; a topoisomerase inhibitor, including but not limited to, an alkyl chain; a (—COCH$_2$R$^{13}$) group; or a (—C(OH)—CH$_2$R$^{13}$); wherein, $R^{13}$ is a hydrogen (—H) group or a hydroxyl group (—OH); a methoxy group (—OCH$_3$); an alkoxy group having 1–20 carbon atoms; an alkyl group having 1–20 carbon atoms; an aryl group having 1–20 carbon atoms; a fatty acyl group having the general structure (—O—CO(CH2)$_n$CH$_3$) wherein n=an integer from 1 to about 20; or a fatty acyl group having the general structure (—O—CO(CH2)$_l$(CH=CH)$_m$(CH2)$_n$CH$_3$) wherein l is an integer between 1 to 3, m is an integer between 1 and about 6, and n is an integer between 1 to about 9; or a chain(R) such as —OCO—(CH$_2$)$_n$—CH$_2$NH$_2$; or OCO—(CH$_2$)$_n$—CO$_2$H and its salts; each of $R^2$ and $R^3$ is, independently of the other, a hydrogen (—H), a hydroxyl group (—OH); a methoxy group (—OCH$_3$); $R^4$ is a hydrogen (—H) group; a methoxy group (—OCH$_3$); a hydroxyl group (—OH); or a halide; each of $Y^1$ and $Y^2$ is, independently of the other, a double bonded oxygen, sulphur, or nitrogen atom; Z is a —H; —OH; a —CO$_2$H group; or a —CO$_2$R group; $R^7$, $R^8$, are, independently, —H; —OH; a halide; —OR$^{19}$; —SH; —SR$^{19}$; —NH$_2$; —NHR$^{19}$; —N(R$^{19}$)$_2$; —CH$_3$; and $R^7$ can additionally be a saccharide; wherein $R^{19}$ is an alkyl chain; an alkylating moiety; a cycloalkyl chain; a cyclic ring; or a hydrogen; $R^9$ can be —H; —CH$_3$; alkyl; aryl; CH$_2$OH, CH$_2$F; $R^{10}$, $R^{11}$ and $R^{12}$ are, independently, —H; —OH; a halide; —OR; —SH; —SR; —NH$_2$; —NHR; —N(R)$_2$; —CH$_3$; one of $R^5$ and $R^6$ is a —H; one of $R^5$ and $R^6$ is a X-alkyl-aromatic-ring (AAR) substituent such as —XAAR, wherein, A is an alkyl group and wherein, AR is an substituted phenyl ring; or a substituted five-member ring; or a heteroatomic five-member ring; or a heteroatomic six-member ring such as a pyridine ring; of the form;

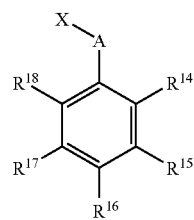

wherein, $R^{14}$–$R^{18}$ are independently a (—H) group; a hydroxyl group (—OH); a methoxy group (—OCH$_3$); a nitro group (—NO$_2$), an amine group (—NH$_2$), a halide; an alkoxy group having 1–20 carbon atoms; an alkyl group having 1–20 carbon atoms; an aryl group having 1–20 carbon atoms; an alkyl-amino group; an alkyl-thio group; a cyano group (CN, SCN); an —CO$_2$H group; an —CO$_2$R group; and the aromatic ring may be disubstituted, trisubstituted, tetrasubstituted or pentasubstituted; and X is a —O, —N or —S, or —SO, or —SO$_2$ group; and A is (CH$_2$)$_n$ where n=0, 1, 2, 3, 4, 5, 6, 7, 8, 9, or 10, wherein, if $R^5$ is a XAAR substituent $R^6$ is not and if $R^6$ is a XAAR substituent $R^5$ is not.

In other specific embodiments, the C-4' substituted anthracycline compounds of the present invention have the general formula:

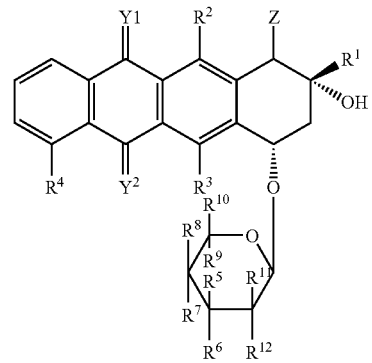

wherein, $R^1$ denotes any suitable group or combination of groups that form but are not limited to a nucleic acid intercalator or binding compound; a topoisomerase inhibitor, including but not limited to, an alkyl chain; a (—COCH$_2$R$^{13}$) group; or a (C(OH)—CH$_2$R$^{13}$) wherein, $R^{13}$ is a hydrogen (—H) group or a hydroxyl group (—OH); a methoxy group (—OCH$_3$); an alkoxy group having 1–20 carbon atoms; an alkyl group having 1–20 carbon atoms; an aryl group having 1–20 carbon atoms; a fatty acyl group having the general structure(—O—CO(CH$_2$)$_n$CH$_3$) wherein n=an integer from 1 to about 20; or a fatty acyl group having the general structure (—O—CO(CH2)$_l$(CH=CH)$_m$(CH2)$_n$CH$_3$), wherein l is an integer between 1 to 3, m is an integer between 1 and about 6, and n is an integer between 1 to about 9; or a chain(R) such as —OCO—(CH$_2$)$_n$—CH$_2$NH$_2$; or OCO—(CH$_2$)$_n$—CO$_2$H and its salts; each of $R^2$ and $R^3$ is, independently of the other, a hydrogen (—H), a hydroxyl group (—OH); a methoxy group (—OCH$_3$); $R^4$ is a hydrogen (—H) group; a methoxy group (—OCH$_3$); a hydroxyl group (—OH); or a halide; each of $Y^1$ and $Y^2$ is, independently of the other, a double bonded oxygen, sulphur, or nitrogen atom; Z is a —H; —OH; a —CO$_2$H group; or a —CO$_2$R group; $R^5$, $R^6$, are, independently, —H; —OH; a halide; —OR$^{19}$; —SH; —SR$^{19}$; —NH$_2$; —NHR$^{19}$; —N(R$^{19}$)$_2$; —CH$_3$; wherein $R^{19}$ is an alkyl chain; an alkylating moiety; a cycloalkyl chain; a cyclic ring; or a hydrogen; and $R^6$ can additionally be a an alkylating moiety; $R^9$ can be —H; —CH$_3$; alkyl; aryl; CH$_2$OH, CH$_2$F; $R^{10}$, $R^{11}$ and $R^{12}$ are, independently, —H; —OH; a halide; —OR; —SH; —SR; —NH$_2$; —NHR; —N(R)$_2$; —CH$_3$; one of $R^7$ and $R^8$ is a —H; one of $R^7$ and $R^8$ is a X-alkyl aromatic-ring (AAR) substituent such as —XAAR, wherein, A is an alkyl group and wherein, AR is an unsubstituted phenyl ring; or a substituted phenyl ring; or a substituted five-member ring such as a pyridine ring; or a heteroatomic five-member ring, of the general form;

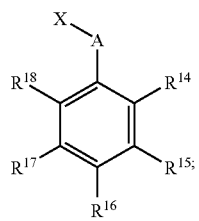

wherein, $R^{14}$–$R^{18}$ are independently a (—H) group; a hydroxyl group (—OH); a methoxy group (—OCH$_3$); a nitro group (—NO$_2$), an amine group (—NH$_2$), a halide; an alkoxy group having 1–20 carbon atoms; an alkyl group having 1–20 carbon atoms; an aryl group having 1–20 carbon atoms; an alkyl-amino group; an alkyl-thio group; a cyano group (CN, SCN); an —CO$_2$H group; an —CO$_2$R group; and the aromatic ring may be disubstituted, trisubstituted, tetrasubstituted or pentasubstituted; and X is a —O, —N or —S, or —SO, or —SO$_2$ group; and A is (CH$_2$)$_n$ where n=0, 1, 2, 3, 4, 5, 6, 7, 8, 9 or 10; wherein if $R^7$ is a XAAR substituent $R^8$ is not and if $R^8$ is a XAAR substituent $R^7$ is not.

Certain specific embodiments of the anthracyclines of the invention are shown in FIGS. 2–25.

The present application also comprises methods of preparing novel substituted sugar substrates and their use in the synthesis of the novel anthracycline analogs described in this invention. In certain embodiments the method for the synthesis of 4'-O-benzylated sugars is described. These 4-O-benzylated sugars may comprise one of two main classes; glycal sugars or 1-O-silyalated sugars. Examples of the benzylated sugars encompassed by this invention are WP567, WP735, WP736, WP819, WO820, WP821, WP822, WP823, WP824 and WP825.

Related embodiments describe the method for synthesizing glycals using various bases including but not limited to NaH. Other related embodiments describe the synthesis of glycals using various solvents including but not limited to DMF. Yet other related embodiments describe the synthesis of glycals using various alkylating agents including but not limited to benzyl chloride and benzyl bromide.

In certain embodiments, the method for the synthesis of amine containing analogs of anthracyclines is described. Further embodiments describe the use of substituted sugar azides for the synthesis of said amine containing anthracyclines wherein the azido substitution can be at the 1', 2', 3', 4' or 5' position on the sugar. The azide group serves as a masked or neutral form of amine substituent allowing for a coupling reaction (explained in Example 2, Procedure A). This allows the generation of selective conditions to reduce azides (explained in Example 2, Procedure B). In one example the amine containing anthracyclines synthesized by this procedure are 14-OH analogs similar to doxorubicin, epirubicin or daunorubicin such as WP744 and WP769. The azido sugar used in the preparation of this compound is WP819 (explained in Example 1, Procedure A and B).

This procedure also allows the use of 14-O-blocked aglycons as these blocked groups survive the steps in which azides are reduced and can be selectively removed at a later stage (Example 2, Procedure B).

The present application comprises methods of preparing substituted anthracyclines and the preparation of important sugar substrates. In devising the synthetic schemes and compounds of the present invention, the inventors have created a variety of novel compounds. These compounds and their methods of synthesis are described elsewhere in the specification, examples and figures and are given "WP" numbers. The structure of a compound designated with a "WP" number is ascertainable by reviewing the specification and figures. Exemplary specific anthracycline compounds that are encompassed by the invention are WP831, WP791, WP790, WP787, WP786, WP785, WP784, WP780, WP778, WP775, WP774, WP765, WP764, WP758, WP757, WP756, WP755, WP799, WP797, WP794, WP783, WP750, WP744, WP727 and WP571. Exemplary specific sugar substrates that are encompassed by the invention are WP567, WP735, WP736, WP819, WP820, WP821, WP822, WP823, WP824, WP825.

The invention also considers methods of treating a patient with cancer, comprising administering to the patient a therapeutically effective amount of the contemplated substituted anthracycline compounds and therapeutic kits comprising, in suitable container means, a pharmaceutically acceptable composition comprising the contemplated substituted anthracycline compounds.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Structure of Doxorubicin and Daunorubicin
FIG. 2. Structure of WP831
FIG. 3. Structure of WP791
FIG. 4. Structure of WP790
FIG. 5. Structure of WP787
FIG. 6. Structure of WP786
FIG. 7. Structure of WP785
FIG. 8. Structure of WP784
FIG. 9. Structure of WP780
FIG. 10. Structure of WP778
FIG. 11. Structure of WP775
FIG. 12. Structure of WP774
FIG. 13. Structure of WP758
FIG. 14. Structure of WP757
FIG. 15. Structure of WP756
FIG. 16. Structure of WP755
FIG. 17. Structure of WP799
FIG. 18. Structure of WP797
FIG. 19. Structure of WP794
FIG. 20. Structure of WP783
FIG. 21. Structure of WP750
FIG. 22. Structure of WP744
FIG. 23. Structure of WP727
FIG. 24. Structure of WP567
FIG. 25. Structure of WP793
FIG. 26. Structure of WP819
FIG. 27. Structure of WP820
FIG. 28. Structure of WP821
FIG. 29. Structure of WP822
FIG. 30. Structure of WP823
FIG. 31. Structure of WP824
FIG. 32. Structure of WP825
FIG. 33. Structure of WP764
FIG. 34. Structure of WP765
FIG. 35. Synthesis of 4'-O-Benzylated Anthracyclines from 4-O-Benzylated glycals FIG. 36. Synthesis of 4'-O-Benzyl-3'-Amino-Anthracyclines FIG. 37. Synthesis of 4-O-Benzyl-Glycals and its 3-O-Derivatives FIG. 38. Synthesis of 4'-O-Benzyl-3'-Deamino-Anthracyclines from 1-O-silylated 4-O-Benzyl-Hexopyranoses FIG. 39. Examples of Selective Alkylation of Acylated Glycals FIG. 40. Synthesis of 3'-Azido-Sugars and its 4-O-Benzylated Derivatives FIG. 41. Alternative Synthesis of 3-Azido-4-O-Benzyl-Daunosamine from 3-Azidoacosamine FIG. 42. Structure of WP735

FIG. 43. Structure of WP736

DESCRIPTION OF ILLUSTRATIVE EMBODIMENTS

Figure 35:
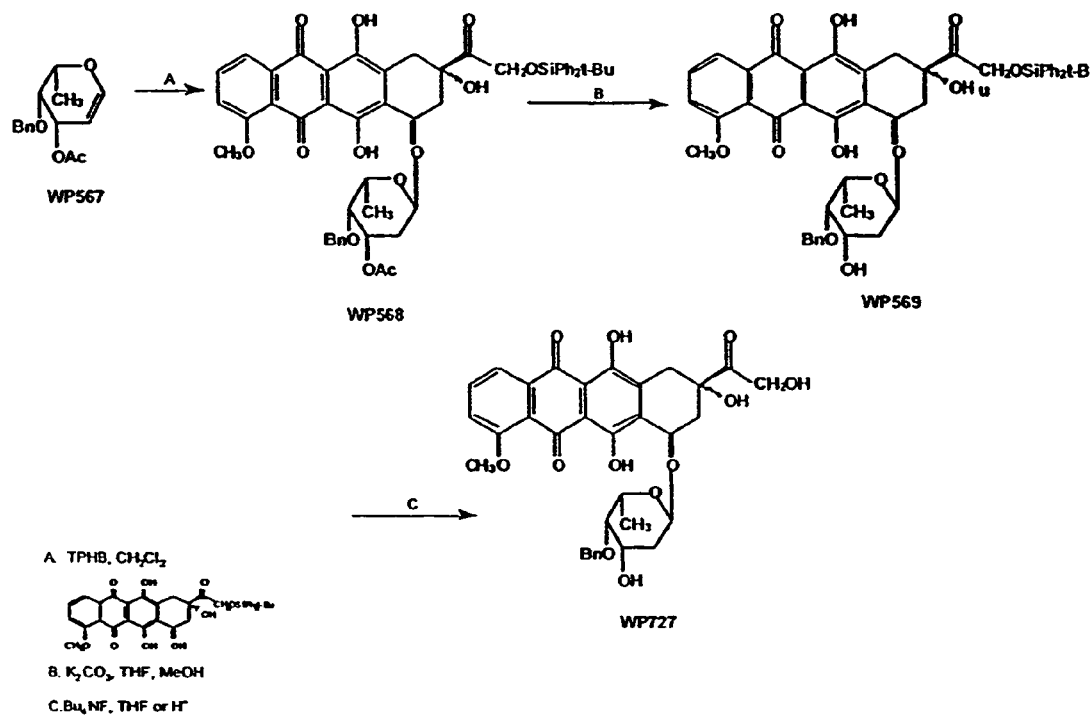

The present invention provides new and novel DNA intercalating agents. These agents are substituted anthracyclines. These compounds show high activity against resistant tumors and cells. A novel approach of the invention produces compounds that are as active or more so than the parent compounds. Furthermore, the inventors' discovery is also for the design of effective DNA-binding substituted anthracyclines.

The anthracycline compounds have a tetracycline ring structure with sugars attached by a glycosidic linkage. Cytotoxic agents of this class have quinone and hydroquinone moieties that permit them to function as electron-accepting and electron donating agents. Doxorubicin and daunorubicin are examples of compounds of this class (FIG. 1). These compounds act by intercalating with DNA. Examples of exemplary anthracyclinones and anthracyclines are given in Table 1.

TABLE 1

List of Exemplary anthracyclinones and anthracyclines.

Anthracyclinones

Rhodomycinone
Isorhodomycinone
Pyrromycinone
4-Demethoxydaunomycinone
4-Demethoxyadriamycinone
Daunomycinone
Adriamycinone Anthracyclines Daunorubicin
Doxorubicin
Epirubicin
Idarubicin
Pyrromycin
Aclacinamycine
Isorhodomycine
Carminomycine
Doxorubicine 14-esters:
Doxorubicin 14-acetate
Doxorubicin 14-propionate
Doxorubicin 14-octanoate
Doxorubicin 14-benzoate
Doxorubicine 14-phenylacetate
4'-Epidaunorubicin
4'-Epidoxorubicin
4'-Iododaunorubicin
4'-Iododoxorubicin
4'-Deoxydaunorubicin
4'-Deoxydoxorubicin
3'-Hydroxydaunorubicin
3'-Hydroxydoxorubicin TABLE 1-continued List of Exemplary anthracyclinones and anthracyclines.

4-Demethoxydaunorubicin
4-Demethoxydoxorubicin
4'-Epi-4-demethoxydaunorubicin
4'-Epi-4-demethoxydoxorubicin Following long-standing patent law convention, the words "a" and "an", when used in the specification including the claims, denotes one or more.

"Aryl" may be a phenyl or alkyl group, unsubstituted or substituted with an amine, alkylamine, nitro, carboxy, sulfonic acid, hydroxy, oxyalkyl, or halide.

The term "saccharide" includes oxidized, reduced or substituted saccharides. Saccharides of this invention include, but are not limited to, ribose, arabinose, xylose, lyxose, allose, altrose, glucose, mannose, fructose, glucose, idose, galactose, talose, ribulose, sorbose, tagatose, gluconic acid, glucuronic acid, glucaric acididuronic acid rhamnose, fucose, N-acetyl glucosamine, N-acetyl galactosamine, N-acetyl neuraminic acid, sialic acid, derivatives of saccharides such as acetals, amines, and phosphorylated sugars, oligosaccharides, as well as open chain forms of various sugars, and the like.

An individual skilled in the art of organic synthesis in light of the present disclosure is able to prepare a large variety of substituted sugars and substituted anthracyclines having C-3'-substituents or having C-4'-substitutents which are expected to have chemotherapeutic activities and may be used in the treatment of cancer and/or other diseases. Exemplary substituted anthracyclines having C-3' alkylated anthracyclines modified at benzyl ring of the present invention are WP831, WP791, WP790, WP787, WP786, WP785, WP784, WP780, WP778, WP775, WP774, WP758, WP757, WP756, WP755 (FIGS. 2–16). Exemplary substituted anthracyclines having 4'-substituted-benzylated anthracyclines of the present invention are WP799, WP797, WP794, WP783, WP750, WP744, WP727 and WP571 (FIGS. 17–25). Such specific anthracyclines having C-3' substituted moieties or having C4'-substituted moieties have been synthesized by the inventors and have been analyzed and the structure confirmed by n.m.r and elemental analysis. The methods of the present application enable one of skill in the art to synthesize these compounds and many other related compounds without undue experimentation.

The present discoveries may be utilized in conjunction with certain techniques that are well-known in the biological arts and that are further described in the following sections.

Pharmaceutical Compositions

The anti-tumor compounds of this invention can be administered to kill tumor cells by any method that allows contact of the active ingredient with the agent's site of action in the tumor. They can be administered by any conventional methods available for use in conjunction with pharmaceuticals, either as individual therapeutically active ingredients or in a combination of therapeutically active ingredients. They can be administered alone but are generally administered with a pharmaceutically acceptable carrier selected on the basis of the chosen route of administration and standard pharmaceutical practice.

Aqueous compositions of the present invention will have an effective amount of anthracycline to kill or slow the growth of cancer cells. Further the potential recognition of genes can be accomplished by the synthesis of substituted anthracyclines having C-3' alkylated anthracyclines modified at benzyl ring and having 4'-substituted-benzylated anthracyclines with specific structures that allow for the recognition of specific parts of DNA. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

A. Parenteral Administration

The active compounds will often be formulated for parenteral administration, e.g., formulated for injection via the intravenous, intramuscular, subcutaneous, or even intraperitoneal routes. The preparation of an aqueous composition that contains an anthracycline of the present invention as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some forms, it will be desirable to formulate the novel compounds in salt form, generally to improve the solubility and bioavailability and to provide an active drug form more readily assimilated. As used herein, the term "pharmaceutically acceptable salt" refers to compounds which are formed from acidifying a substituted anthracycline solution with suitable physiologically tolerated acids. Suitable physiologically tolerated acids are organic and inorganic acids, such as hydrochloric acid, sulfuric acid, phosphoric acid, acetic acid, citric acid, oxalic acid, malonic acid, salicylic acid, maleic acid, methane sulfonic acid, isothionic acid, lactic acid, gluconic acid, glucuronic acid, amidosulfuric acid, benzoic acid, tartaric acid and pamoaic acid. Typically, such salt forms of the active compound will be provided or mixed prior to use.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts and which are formed with inorganic acids such as, for example, hydrochloric or phosphoric acids, or such organic acids as acetic, oxalic, tartaric, mandelic, and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in creams and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

B. Oral Administration

In certain embodiments, active compounds may be administered orally. This is contemplated for agents which are generally resistant, or have been rendered resistant, to proteolysis by digestive enzymes. Such compounds are contemplated to include all those compounds, or drugs, that are available in tablet form from the manufacturer and derivatives and analogues thereof.

For oral administration, the active compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The anthracycline analogs described in the present invention may be administered alone or with cyclodextrins, or substituted cyclodextrin formulations.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Upon formulation, the compounds will be administered in a manner compatible with the dosage formulation and in such amount as is therapeutically effective. The formulations are easily administered in a variety of dosage forms, such as those described below in specific examples.

Therapies

One of the major challenges in oncology today is the effective treatment of a given tumor. Tumors are often resistant to traditional therapies. Thus, a great deal of effort is being directed at finding efficous treatment of cancer. One way of achieving this is by combining new drugs with the traditional therapies and is discussed below. In the context of the present invention, it is contemplated that therapies using the anthracycline analogs could be used in conjunction with surgery, chemotherapy, radiotherapy and indeed gene therapeutic intervention. It also may prove effective to combine the anthracycline analog based chemotherapy with antisense or immunotherapies directed at tumor marker.

"Effective amounts" are those amounts of a candidate substance effective to reproducibly inhibit decrease, reduce, inhibit or otherwise abrogate the growth of a cancer cell in an assay in comparison to levels in untreated cells.

A. Standard Therapies a. Chemotherapy: A variety of chemical compounds, also described as "chemotherapeutic agents", function to induce DNA damage, are used to treat tumors. Chemotherapeutic agents contemplated to be of use, include, adriamycin, 5-fluorouracil (5FU), etoposide (VP-16), camptothecin, actinomycin-D, mitomycin, cisplatin (CDDP), hydrogen peroxide, carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, tamoxifen, taxol, transplatinum, vincristin, vinblastin and methotrexate to mention a few.

Agents that damage DNA include compounds that interfere with DNA replication, mitosis and chromosomal segregation. Such chemotherapeutic compounds include adriamycin, also known as doxorubicin, etoposide, verapamil, podophyllotoxin; and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. A number of such agents have been developed, particularly useful are agents that have undergone extensive testing and are readily available. 5-fluorouracil (5-FU), is one such agent that is preferentially used by neoplastic tissue, making it particularly useful for targeting neoplastic cells. Thus, although quite toxic, 5-FU, is applicable with a wide range of carriers, including topical and even intravenous administrations with doses ranging from 3 to 15 mg/kg/day.

Agents that directly cross-link nucleic acids, specifically DNA, are envisaged to facilitate DNA damage leading to a useful antineoplastic treatment. For example, cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

b. Radiotherapy: Radiotherapeuticagents and factors include radiation and waves that induce DNA damage for example, γ-irradiation, X-rays, UV-irradiation, microwaves, electronic emissions, radioisotopes,and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

c. Surgery: Surgical treatment for removal of the cancerous growth is generally a standard procedure for the treatment of tumors and cancers. This attempts to remove the entire cancerous growth. However, surgery is generally combined with chemotherapy and/or radiotherapy to ensure the destruction of any remaining neoplastic or malignant cells.

B. Combination Therapies

To kill cells, inhibit cell growth, inhibit metastasis, inhibit angiogenesis or otherwise reverse or reduce the malignant phenotype of tumor cells, the methods of standard therapy discussed above are generally insufficient as tumors are often resistant to several of these agents. Often combining a host of different treatment methods prove most effective in cancer therapy. Further, several AIDS afflicted patients have a higher risk of developing cancers. Combination therapy in these cases is required to treat AIDS as well as the cancer. Using the methods and compounds developed in the present invention, one would generally contact a "target" cell with an anthracycline analog synthesized in the present invention and at least one other agent. These compositions would be provided in a combined amount effective to kill or inhibit proliferation of the cell. This process may involve contacting the cells with the an anthracycline analog synthesized in the present invention and the other agent(s) or factor(s) at the same time. This may also be achieved by contacting the cell with a single composition or pharmacological formulation that includes both agents, or by contacting the cell with two distinct compositions or formulations, at the same time, wherein one composition includes the anthracycline analogs synthesized herein and the other includes the agent.

Alternatively, the anthracycline analog-based treatment may precede or follow the other agent treatment by intervals ranging from minutes to weeks. In embodiments where the other agent and anthracycline analog-based therapy are applied separately to the cell, one would generally ensure that a significant period of time did not expire between the time of each delivery, such that the agent and anthracycline analog-based treatment would still be able to exert an advantageously combined effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either anthracycline analog-based treatment or the other agent will be desired. Various combinations may be employed, where anthracycline analog-based treatment is "A" and the other agent is "B", as exemplified below:

N/B/A B/NB B/B/A A/A/B B/A/A A/B/B B/B/B/A B/B/ A/B
A/NB/B NB/A/B NB/B/A B/B/A/A B/NB/A B/A/A/B B/B/B/A
A/A/NB B/A/A/A NB/A/A A/NB/A A/B/B/B B/NB/B B/B/NB

Other combinations are also contemplated. Again, to achieve cell killing, both agents are delivered to a cell in a combined amount effective to kill the cell.

The invention also encompasses the use of a combination of one or more DNA damaging agents, whether chemotherapeutic compounds or radiotherapeutics as described in the section above, together with the anthracycline analog. The invention also contemplates the use of the anthracycline analog in combination with surgical removal of tumors to treat any remaining neoplastic or metastasized cells. Further, immunotherapy may be directed at tumor antigen markers that are found on the surface of tumor cells. The invention also contemplates the use of C-3' and C-4' substituted anthracycline analog-based treatments in combination with gene therapy, directed toward a variety of oncogenes, such as, tumor markers, cell cycle controlling genes. For example, combining the anthracycline analog-based treatment and gene therapy towards oncogenes such as p53, p16, p21, Rb, APC, DCC, NF-1, NF-2, BCRA2, p16, FHIT, WT-1, MEN-I, ME-II, BRCA1, VHL, FCC, MCC, ras, myc, neu, raf, erb, src, fms, jun, trk, ret, gsp, hst, bcl and abl mutations.

The other agent may be prepared and used as a combined therapeutic composition, or kit, by combining it with the anthracycline analog-based treatment, as described above. The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It is proposed that the regional delivery of anthracycline analog-based drugs described in the present invention to patients with tumors will be a very efficient method for delivering a therapeutically effective chemical to counteract the clinical disease. Similarly, other chemotherapeutics, radiotherapeutics, gene therapeutic agents may be directed to a particular, affected region of the subjects body. Alternatively, systemic delivery of anthracycline analog-based treatment and/or the agent may be appropriate in certain circumstances, for example, where extensive metastasis has occurred.

It also should be pointed out that any of the standard or other therapies may prove useful by themselves in treating a cancer. In this regard, reference to chemotherapeutics and anthracycline analog-based treatment in combination should also be read as a contemplation that these approaches may be employed separately.

When such combination therapy is employed for the treatment of a tumor, the cytotoxic agent may be administered at a dosage known in the art to be effective for treating the tumor. However, the anthracycline analog-based compounds may produce an additive or synergistic effect with a cytotoxic agent against a particular tumor. Thus, when such combination therapy is used, the dosage of anthracycline analog-based drugs administered may be less than that administered when the cytotoxic agent is used alone. Similarly, for patients afflicted by AIDS, AZT/protease inhibitors will be used with anthracycline analog compounds, or other herein mentioned therapeutic agent(s). Again the dosage of anthracycline analog-based compounds or other conjunctively utilized agent, may be altered to suit the AIDS treatment.

Preferably, the patient is treated with anthracycline analog-based compounds for about 1 to 14 days, preferably 4 to 14 days, prior to the beginning of therapy with a cytotoxic agent, and thereafter, on a daily basis during the course of such therapy. Daily treatment with the anthracycline analogs can be continued for a period of, for example, 1 to 365 days after the last dose of the cytotoxic agent is administered.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

Synthesis of Exemplary Substituted Anthracyclines having C-3' Alkylated Anthracyclines Modified at Benzyl Ring General Procedure for Making C-3' Alkylated Anthracyclines Modified at Benzyl Ring A. Synthesis of 3'-N-nonitro benzyl derivatives of daunorubicin and 4-demethoxy-daunorubicin:

1. Procedure A

Daunorubicin (1 mmol), 4-nitrobenzyl bromide (1 mmol), and sodium carbonate (250 g) were dissolved in DMF (10 ml). Dichloromethane (10 ml) was added to this solution, and obtained mixture was stirred at room temperature until all substrate was converted into the product. (monitored by TLC). After reaction was completed the reaction mixture was diluted with dichloromethane (100 ml), and washed with water until neutral. The organic solution was dried over sodium sulfate, then drying agent was removed and solvent evaporated under diminished pressure, and product was purified by column chromatography (Silica Gel 60 Merck), using chloroform, chloroform/methanol 98:2, 95:5 as an eluent.

1.1 The Following Compounds were Obtained from Daunorubicin According the above Procedure (Procedure A):

(i) WP 756 FIG. 15

$^1$H-n.m.r (CDCl$_3$) δ: 13.99, 13.40 (2s, 1H ea, 6,11-OH), 8.05 (d, 1H, J=7.5 Hz, H-1), 7.93 (d, 1H, J=8.1 Hz, H-2), 7.80 (dd, 1H, J=8.2 Hz, H-3), 7.60–7.52 (m, 2H, H-aromatic), 7.44–7.40 (m, 2H, H-aromatic), 5.54 (d, J=3.2 Hz, H-1'), 5.32 (, 1H, H-7), 4.67 (s, 1H, 9-OH), 4.13–4.06 (m, 4H, OMe and H-5'), 4.04 (d, 1H, J=13.6 Hz, Ch2Ph), 3.95 (d, 1H, J=13.6 Hz, Ch2Ph), 3.72(,1H, H-4'), 3.25 (dd, 1H, J=18.1 Hz, J=1.1 Hz, H=10), 2.97 (d, 1H, J=18.9 Hz, H-10), 3.00–2.92 (m, 1H, H-3'), 2.44 (s, 3 H, 14-CH$_3$), 2.38 (d, 1H, J=14.82 Hz, H-8), 2.12 (dd, 1H, J=14.8 Hz, J=4.0 Hz, H-8), 1.86–1.69 (m, 2H, H-2'a,e), 1.4 (d, 3H, J=6.6 Hz, H-6').

Anal. Elem. Calcd. for: C$_{34}$H$_{35}$O$_{12}$N$_2$Cl×1.5 H$_2$O: C, 56.24; H, 5.27; N, 3.86; Cl, 4.88. Found: C: 56.24; H: 5.27; N: 3.86; Cl: 4.88.

(ii) WP 784 FIG. 8

$^1$H-n.m.r (CDCl$_3$) δ: 13.98, 13.29 (2s, 1H ea, 6,11-OH), 8.14 (s, 1H, H-aromatic), 8.08 (d, 1H, J=8.1 Hz, H-arom), 8.03 (d, 1H, J=7.6 Hz, H-1), 7.78 (dd, 1H, J=J=8.15 Hz H-2), 7.62 (d, 1H, J=7.6 Hz, H-aromatic), 7.46 (dd, 1H, J=J=7.9 Hz, H-aromatic), 7.39 (d, 1H, J=8.4 Hz, H-aromatic) 5.53 (d, J=3.0 Hz, H-1'), 5.3 (, 1H, H-7), 4.62 (s, 1H, 9-OH), 4.10–4.08 (m, 1H, H-5'), 4.08 (s, 3H, OMe), 3.9 (d, 1H, J=13.6 Hz, Ch2Ph), 3.81 (d, 1H, J=13.6 Hz, Ch2Ph), 3.67 (, 1H, H-4'), 3.22 (dd, 1H, J=18.8 Hz, J=1.8 Hz, H=10), 2.96 (d, 1H, J=18.8 Hz, H-10), 2.96–2.92 (m, 1H, H-3'), 2.41 (s, 3 H, 14-CH$_3$), 2.36 (d, 1H, J=14.8 Hz, H-8), 2.11 (dd, 1H, J=14.8 Hz, J=2.1 Hz, H-8), 1.82–1.75 (m, 2H, H-2'a,e), 1.37 (d, 3H, J=6.5 Hz, H-6').

Anal. Elem. Calcd. for: C$_{34}$H$_{35}$O$_{12}$N$_2$Cl×1.5 H$_2$O: C: 56.24; H: 5.27; N: 3.86; Cl: 4.88. Found: C: 55.94; H: 5.27; N: 3.78; Cl: 4.92.

(iii) WP 755 FIG. 16

$^1$H-n.m.r (CDCl$_3$) δ: 14.02, 13.30 (2s, 1H ea, 6,11-OH), 8.17 (d, 1H, J=8.6 Hz, H-aromatic), 8.05 (d, 1H, J=7.8 Hz, H-1), 7.81 (dd, 1H, J=J=7.8 Hz, H-2), 7.49–7.41 (m, 4H, H-3 and H-aromatic), 5.54 (s, 1H, H-1'), 5.32 (, 1H, H-7), 4.64 (s, 1H, 9-OH), 4.11 (s, 3H, OMe), 4.09 (q, 1H, J=6.5 Hz, H-5'), 3.93 (d, 1H, J=14 Hz, Ch2Ph), 3.83 (d, 1H, J=14 Hz, Ch2Ph), 3.67 (, 1H, H-4'), 3.25 (d, 1H, J=18.9 Hz, H=10), 2.98 (d, 1H, J=18.9 Hz, H-10), 2.96–2.92 (m, 1H, H-3'), 2.43 (s, 3 H, 14-CH$_3$), 2.38 (d, 1H, J=15.2 Hz, H-8), 2.13 (dd, 1H, J=15.2 Hz, J=4.13 Hz, H-8), 1.82–1.78 (m, 2H, H-2'a,e), 1.38 (d, 3H, J=6.6 Hz, H-6').

Anal. Elem. Calcd. for: C$_{34}$H$_{35}$O$_{12}$N$_2$Cl×H$_2$O: C: 56.95; H: 5.2; N: 3.91; Cl: 4.94. Found: C, 56.99; H, 5.19; N, 3.81; Cl, 4.89.

1.2 The Following Compounds were Obtained from 4-demethoxy-daunorubicin using Procedure A:

(iv) WP 790 FIG. 4

$^1$H-n.m.r (CDCl$_3$) δ: 13.58, 13.34 (2s, 1H ea, 6,11-OH), 8.36–8.32 (m, 2H, H-1,4), 8.90 (d, 1H, J=8.2 Hz, H-arom), 7.85–7.80 (m, 2H, H-2,3), 7.57 (dd, 1H, J=J=7.5 Hz, H-aromatic), 7.51 (d, 1H, J=6.5 Hz, H-aromatic), 7.40 (dd, 1H, J=J=7.1 Hz, H-aromatic), 5.50 (d, 1H, J=3.6 Hz, H-1'), 5.28 (, 1H, H-7), 4.66 (s, 1H, 9-OH), 4.10 (m, 1H, J=6.6 Hz, H-5'), 4.03 (d, 1H, J=14.7 Hz, Ch2Ph), 3.94 (d, 1H, J=14.7 Hz, Ch2Ph), 3.70 (, 1H, H-4'), 3.25 (dd, 1H, J=19 Hz, J=1.7 Hz, H=10), 3.00 (d, 1H, J=19 Hz, H-10), 2.96–2.91 (m, 1H, H-3'), 2.40 (s, 3H, 14-CH$_3$), 2.38 (d, 1H, J=14.9 Hz, H-8), 2.10 (dd, 1H, J=14.9 Hz, J=4.1 Hz, H-8), 1.82 (ddd, 1H, J=13.3 Hz, J=4.2 Hz, H-2'a), 1.74 (dd, 1H, J=13.3 Hz, J=4.9 Hz, H-2'e), 1.38 (d, 3H, J=6.6 Hz, H-6').

Anal. Elem. Calcd. for: C$_{33}$H$_{33}$O$_{11}$N$_2$Cl×1.5 H$_2$O: C: 56.94; H: 5.21; N: 4.02; Cl: 5.09. Found: C: 57.00; H: 5.13; N: 3.98; Cl: 5.16.

(v) WP 774 FIG. 12

$^1$H-n.m.r (CDCl$_3$) δ: 13.59, 13.35 (2s, 1H ea, 6,11-OH), 8.37–8.32 (m, 2H, H-1,4), 8.13 (d, 1H, J=8.2 Hz, H-arom), 7.86–7.82 (m, 2H, H-2,3), 7.44 (d, 2H, H-aromatic), 5.50 (s, 1H, H-1'), 5.28 (, 1H, H-7), 4.62 (s, 1H, 9-OH), 4.09 (m, 1H, J=6.4 Hz, H-5'), 3.91 (d, 1H, J=14.7 Hz, Ch2Ph), 3.83 (d, 1H, J=14.7 Hz, Ch2Ph), 3.66 (, 1H, H4'), 3.25 (dd, 1H, J=19 Hz, J=1.8 Hz, H=10), 2.98 (d, 1H, J=19 Hz, H-10), 2.96–2.93 (m, 1H, H-3'), 2.40 (s, 3H, 14-CH$_3$), 2.37 (d, 1H, J=13.0 Hz, H-8), 2.11 (dd, 1H, J=13.0 Hz, J=4.0 Hz, H-8), 1.84–1.76 (m, 2H, H-2'a,e), 1.28 (d, 3H, J=6.4 Hz, H-6').

Anal. Elem. Calcd. for: C$_{33}$H$_{33}$O$_{11}$N$_2$Cl×0.5 H$_2$O: C: 57.15; H: 4.87; N: 4.04; Cl: 5.11. Found: C: 57.15; H: 5.08; N: 4.01; Cl: 5.11.

1.3 The Following Compound WP787 was Obtained when 4-amino-daunorubicin using benzyl bromide According to Procedure A:

(vi) WP 787 FIG. 5

$^1$H-n.m.r (CDCl$_3$) δ: 13.98, 13.29 (2s, 1H ea, 6,11-OH), 8.02 (d, 1H, J=7.3 Hz, H-1), 7.81 (dd, 1H, J=7.8 Hz, H-2), 7.40 (d, 1H, J=8.1 Hz, H-3), 7.35 (s, 4H, H-aromatic), 7.31–7.26 (m, 1H, H-aromatic), 5.42 (d, 1H, J=4.0 Hz, H-1'), 5.25 (, 1H, H-7), 4.64 (s, 1H, 9-OH), 4.14 (q, 1H, J=6.6 Hz, H-5'), 4.11 (d, 1H, J=12.7 Hz, Ch2Ph), 4.07 (s, 3H, OMe), 3.77 (d, 1H, J=12.7 Hz, Ch2Ph), 3.72–3.68 (m, 1H, H-3'), 3.22 (dd, 1H, J=18.8 Hz, J=1.8 Hz, H=10), 2.94 (d, 1H, J=18.8 Hz, H-10), 2.76 (d, 1H, J=3.9 Hz, H-4'), 2.41 (s, 3 H, 14-CH$_3$), 2.29 (d, 1H, J=14.7 Hz, H-8).

Anal. Elem. Calcd. for: C$_{34}$H$_{36}$O$_{10}$NCl: C: 62.43; H: 5.55; N: 2.14; Cl: 5.42.

(vii) WP 831 FIG. 2 The Following Compound was Obtained from Daunorubicin using 4-picolyl Chloride According to Procedure A:

$^1$H-n.m.r (CDCl$_3$) δ: 13.97, 13.37 (2s, 1H ea, 6,11-OH), 8.50 (d, 2H, H-arom), 8.02 (d, 1H, J=7.5Hz, H-1), 7.78 (dd, 1H, J=7.8 Hz, H-2), 7.39 (d, 1H, H-3), 7.18 (m, 2H, H-aromatic), 5.51 (d, 1H, J=3.8 Hz, H-1'), 5.28 (, 1H, H-7), 4.62 (s, 1H, 9-OH), 4.08 (m, 4H, H-5' and OMe), 3.81 (d, 1H, J=14.2 Hz, Ch2Ph), 3.72 (d, 1H, J=14.2 Hz, Ch2Ph), 3.64 (, 1H, H-4'), 3.37 (dd, 1H, J=19 Hz, J=1.5 Hz, H=10), 2.94 (d, 1H, J=19 Hz, H-10), 2.96–2.93 (m, 1H, H-3'), 2.41 (s, 3 H, 14-CH$_3$), 2.36 (d, 1H, J=14.8 Hz, H-8), 2.10 (dd, 1H, J=14.8 Hz, J=4.1 Hz, H-8), 1.83–1.75 (m, 2H, H-2'a,e), 1.36 (d, 3H, J=6.4 Hz, H-6').

Anal. Elem. Calcd. for: C$_{33}$H$_{36}$O$_{10}$N$_2$Cl$_2$×3 H$_2$O: C: 53.16; H: 5.68; N: 3.76; Cl: 9.51. Found: C: 53.70; H:5.59; N: 3.67; Cl: 9.36.

1.4 The Following Compound WP 786 was Obtained According Procedure A using 4-fluorobenzyl bromide as alkylating Agent:

(viii) WP 786 FIG. 6

$^1$H-n.m.r (CDCl$_3$) δ: 13.98, 13.30 (2s, 1H ea, 6,11-OH), 8.03 (d, 1H, J=7.6 Hz, H-1), 7.78 (dd, 1H, J=7.6 Hz, H-2), 7.39 (d, 1H, J=7.8 Hz, H-3), 7.23–7.20 (m, 2H, H-aromatic), 7.00–6.95 (m, 2H, H-aromatic), 5.51 (d, 1H, J=3.7 Hz, H-1'), 5.3 (, 1H, H-7), 4.69 (s, 1H, 9-OH), 4.08 (s, 3H, OMe), 4.06 (q, 1H, J=6.6 Hz, H-5'), 3.96 (d, 1H, J=12.7 Hz, Ch2Ph), 3.64 (d, 1H, J=12.7 Hz, Ch2Ph), 3.64 (, 1H, H-4'), 3.23 (dd, 1H, J=18.9 Hz, J=1.9 Hz, H=10), 2.96(d, 1H, J=18.9 Hz, H-10), 2.96–2.93 (m, 1H, H-3'), 2.42 (s, 3H, 14-CH$_3$), 2.37 (d, 1H, J=13.8 Hz, H-8), 2.09 (dd, 1H, J=13.8 Hz, J=4.1 Hz, H-8), 1.78 (ddd, 1H, J=13.1 Hz, J=4.0 Hz, H-2'a), 1.67 (dd, 1H, J=13.1 Hz, J=4.9 Hz, H-2'e), 1.37 (d, 3H, J=6.6 Hz, H-6').

B. Synthesis of 3'-N-nitro benzyl derivatives of doxorubicin and 4-demethoxydoxorubicin:

2. Procedure B

Doxorubicin having hydroxyl at C-14 protected by sylylation (1 mmol), 4-nitrobenzyl bromide (1 mmol), and sodium carbonate (250 mg) were dissolved in DMF (10 ml). Dichloromethane (10 ml) was added to this solution, and obtained mixture was stirred at room temperature until all substrate was converted into the product. (monitored by TLC control). After reaction was completed the reaction mixture was diluted with di chloromethane (100 ml), and washed with water until neutral. The organic solution was dried over sodium sulfate, then drying agent and solvent were removed, and product was purified by column chromatography (Silica Gel 60 Merck), using chloroform, chloroform/methanol 98:2, as eluent.

Obtained compounds was dissolved in THF (6 ml) and to this 1 N water solution of HCl (9 ml) was added. The mixture was stirred at room temp. overnight, then it was diluted with chloroform, and neutralized with 10% water solution of potassium bicarbonate. Organic solution was dried over sodium sulfate. Drying agent was filtered off, and solvent was evaporated to dryness. Crude product was purified by column chromatography (Silica Gel 60 Merck), using chloroform/methanol 98:2, 95:5 as eluent.

The following compounds were obtained according to this Procedure B:

(ix) WP 780 FIG. 9

$^1$H-n.m.r (CDCl$_3$) δ: 13.96, 13.26 (2s, 1H ea, 6,11-OH), 8.03 (d, 1H, J=7.7 Hz, H-aromatic), 7.91 (d, 1H, J=8.1 Hz, H-1), 7.79 (dd, 1H, J=8.1 Hz, H-2), 7.56 (d, 1H, J=J=7.8 Hz H-aromatic), 7.50 (d, 1H, J=6.8 Hz, H-aromatic), 7.40–7.30 (m, 2H, H-3 and H-aromatic), 5.52 (d, 1H, J=3.6 Hz, H-1'), 5.3 (, 1H, H-7), 4.77 (s, 2H, 14-CH$_2$), 4.75 (s, 1H, 9-OH), 4.08 (s, 3H, OMe), 4.03 (d, 1H, J=13.6 Hz, Ch2Ph), 3.99 (q, 1H, J=6.6 Hz, H-5') 3.93 (d, 1H, J=13.6 Hz, Ch2Ph), 3.70 (, 1H, H-4'), 3.27 (dd, 1H, J=18.9 Hz, J=1.7 Hz, H=10), 3.03 (d, 1H, J=18.9 Hz, H-10), 2.89 (m, 1H, H-3'), 2.36 (d, 1H, J=14.8 Hz, H-8), 2.16 (dd, 1H, J=14.8 Hz, J=2.9 Hz, H-8), 1.84 (ddd, 1H, J=13.1 Hz, J=4.0 Hz, H-2'a), 1.68 (dd, 1H, J=13.1 Hz, J=4.6 Hz, H-2'e), 1.39 (d, 3H, J=6.6 Hz, H-6').

Anal. Elem. Calcd. for: C$_{34}$H$_{35}$O$_{13}$N$_2$Cl×2 H$_2$O: C: 54.37; H:5.23; N: 3.73; Cl: 4.72. Found: C: 54.49; H: 5.13; N: 3.70; Cl: 4.76.

(x) WP 765 FIG. 34

$^1$H-n.m.r (CDCl$_3$) δ: 13.96, 13.24 (2s, 1H ea, 6,11-OH), 8.13 (d, 1H, J=7.6 Hz, H-1), 8.01 (d, 1H, J=7.5 Hz, H-2), 7.71 (d, 1H, J=7.8 Hz, H-3), 7.45–7.40 (m, 4H, H-aromatic), 5.52 (, 1H, H-1'), 5.31 (, 1H, H-7), 4.75 (s, 2H, 14-CH$_2$), 4.70 (s, 11H, 9-OH), 4.00 (s, 3H, OMe), 3.99 (q, 1H, J=6.6 Hz, H-5') 3.91 (d, 1H, J=Hz, Ch2Ph), 3.82 (d, 1H, J=14.0 Hz, Ch2Ph), 3.66 (, 1H, H-4'), 3.24 (d, 1H, J=18.8 Hz, H=10), 3.00 (d, 1H, J=18.8 Hz, H-10), 2.90–2.88 (m, 1H, H-3'), 2.37 (d, 1H, J=14.8 Hz, H-8), 2.15 (dd, 1H, J=14.8 Hz, J=4.0 Hz, H-8), 1.8–1.6 (m, 2H), H-2'a,e), 1.39 (d, 3H, J=6.5 Hz, H-6').

Anal. Elem. Calcd. for: C$_{34}$H$_{35}$O$_{13}$N$_2$Cl×0.5 H$_2$O: C: 59.39; H, 5.13; N: 4.07. Found: C: 59.00; H, 5.15; N: 4.07.

2.1 The Follwing Compound WP778 was obtained from 14-O-silylated 4-demethoxydroxyrubicin Following Compound was Prepared According Procedure B:

(xi) WP 778 FIG. 10

$^1$H-n.m.r (CDCl$_3$) δ: 13.57, 13.30 (2s, 1H ea, 6,11-OH), 8.36–8.32 (m, 2H, H-1,4), 8.13 (d, 2H, J=8.7 Hz, H-arom), 7.88–7.83 (m, 2H, H-2,3), 7.44 (d, 2H, J=8.7 Hz, H-aromatic), 5.52 (d, 1H, J=3.3 Hz, H-1'), 5.30 (, 1H, H-7), 4.76 (, 2H, 14-CH), 4.73 (s, 1H, 9-OH), 4.01 (m, 1H, J=6.6 Hz, H-5'), 3.93 (d, 1H, J=14.1 Hz, Ch2Ph), 3.83 (d, 1H, J=14.1 Hz, Ch2Ph), 3.68 (, 1H, H-4'), 3.29 (dd, 1H, J=19 Hz, J=1.8 Hz, H=10), 3.06 (d, 1H, J=19 Hz, H-10), 2.96–2.88 (m, 1H, H-3'), 2.38 (d, 1H, J=14.7 Hz, H-8), 2.15 (dd, 1H, J=14.7 Hz, J=4.0 Hz, H-8), 1.88–1.74 (m, 1H, H-2'a,e), 1.29 (d, 3H, J=6.6 Hz, H-6').

C. Synthesis of 3' -N-amino-substituted benzyl derivatives of daunorubicin and 4-methoxy-daunorubicin:

3. Procedure C

Products obtained according to the procedure A and B (0.1 mmol) were dissolved in the mixture of dichloromethane and methyl alcohol (1:1 v/v) (10 ml), then stannous chloride (II) (1.1 g) was added and the mixture was stirred at room temp. until all substrate disappeared (TLC control). The reaction mixture was then diluted with chloroform, and saturated solution of sodium bicarbonate (100 ml) was added. The reaction mixture was stirred at room temp. for 3 hr, then the inorganic salts were filtered off, and washed with chloroform. Organic solution was washed with water until neutral, then dried over Na$_2$SO$_4$. Drying agent and solvent were removed, and product was purified by column chromatography (Silica Gel 60 Merck), using chloroform/methanol 98:2, 95:5, 9:1 as an eluent.

Following compounds were prepared according to the Procedure C:

(xii) WP 758 FIG. 13

$^1$H-n.m.r (CDCl$_3$) δ: 13.98, 13.28 (2s, 1H ea, 6,11-OH), 8.04 (d, 1H, J=8.0 Hz, H-1), 7.78 (dd, 1H, J=8.0 Hz, H-2), 7.38 (d, 1H, J=8.0 Hz, H-3), 7.05 (td, 1H, J=7.6 Hz, J=1.3 Hz, H-aromatic), 6.97 (dd, 2H, J=7.8 Hz, J=1.4 Hz, H-aromatic), 6.63 (m, 2H, H-aromatic), 5.51 (, 1H, H-1'), 5.28 (, 1H, H-7), 4.08 (s, 3H, OMe), 4.13–4.08 (q, 1H, J=6.5 Hz, H-5'), 3.82 (d, 1H, J=12.5 Hz, Ch2Ph), 3.73 (, 1H, H4'), 3.71 (d, 1H, J=12.5 Hz, Ch2Ph), 3.23 (dd, 1H, J=18.9 Hz, J=1.7 Hz, H=10), 2.95 (d, 1H, J=18.9 Hz, H-10), 2.99–2.93 (m, 1H, H-3'), 2.44 (s, 3 H, 14-$CH_3$), 2.7 (, 2H, NH, OH), 2.34 (d, 1H, J=14.9 Hz, H-8), 2.10 (dd, 1H, J=14.9 Hz, J=4.1 Hz, H-8), 1.81–1.74 (m, 2H, H-2'a,e), 1.37 (d, 3H, J=6.6 Hz, H-6').

Anal. Elem. Calcd. for: $C_{34}H_{38}O_{10}N_2Cl_2$: C: 57.88, H: 5.43; N: 3.97; Cl: 10.05. Found: C: 57.85; H: 5.44; N: 3.93; Cl: 9.96.

(xiii) WP 757 FIG. 14

$^1$H-n.m.r ($CDCl_3$) δ: 14.00 (, 1H, H-6 or H-11), 8.06 (d, 1H, J=7.7 Hz, H-1), 7.80 (dd, 1H, J=8.1 Hz, H-2), 7.41 (d, 1H, J=7.7 Hz, H-3), 7.05 (d, 2H, J=8.3 Hz, H-aromatic), 6.62 (d, 2H, J=8.3 Hz, H-aromatic), 5.53 (d, 1H, J=3.4 Hz, H-1'), 5.31 (, 1H, H-7), 4.75 (s, 1H, 9-OH), 4.10 (s, 3H, OMe), 4.10 (q, 1H, J=6.5 Hz, H-5'), 3.71 (d, 1H, J=15.0 Hz, Ch2Ph), 3.7 (, 1H, H-4'), 3.58 (d, 1H, J=15.0 Hz, Ch2Ph), 3.28 (dd, 1H, J=19.0 Hz, J=1.0 Hz, H=10), 3.0 (d, 1H, J=19.0 Hz, H-10), 3.02–2.92 (m, 1H, H-3'), 2.45 (s, 3 H, 14-$CH_3$), 2.40 (d, 1H, J=14.9 Hz, H-8), 2.11 (dd, 1H, J=14.4 Hz, J=4.0 Hz, H-8), 1.78 (ddd, 1H, J=12.5 Hz, J=8.6 Hz, J=3.8 Hz, H-2'a), 1.63 (dd, 1H, J=12.5 Hz, J=5.2 Hz, H-2'e) 1.40 (d, 3H, J=6.5 Hz, H-6').

Anal. Elem. Calcd. for: $C_{34}H_{36}O_{10}N_3$: C: 64.55; H: 5.74; N: 4.43. Found: C: 64.27; H: 5.90; N: 4.28.

(xiv) WP 791 FIG. 3

$^1$H-n.m.r ($CDCl_3$) δ: 8.37 (m, 2H, H-1,4), 7.87–7.83 (m, 2H, H-2,3), 7.04 (dd, 1H, J=8.0 Hz, H-aromatic), 6.97 (d, 2H, J=7.1 Hz, H-aromatic), 6.66–6.62 (m, 2H, H-aromatic), 5.51 (d, 1H, J=3.5 Hz, H-1'), 5.29 (, 1H, H-7), 4.67 (s, 1H, 9-OH), 4.11 (q, 1H, J=6.5 Hz, H-5'), 3.80 (d, 1H, J=12.3 Hz, Ch2Ph), 3.7 (, 1H, H-4'), 3.68 (d, 1H, J=12.3 Hz, Ch2Ph), 3.27 (dd, 1H, J=19.0 Hz, J=1.4 Hz, H=10), 3.0 (d, 1H, J=19.0 Hz, H-10), 2.97–2.88 (m, 1H, H-3'), 2.40 (s, 3 H, 14-$CH_3$), 2.37 (d, 1H, J=15.2 Hz, H-8), 2.11 (dd, 1H, J=15.2 Hz, J=4.0 Hz, H-8), 1.89–1.73 (m, 2H, H-2'a,e), 1.35 (d, 3H, J=6.5 Hz, H-6').

(xv) WP 764 FIG. 33

$^1$H-n.m.r (DMSO-d6) δ: 7.91–7.89 (m, 2H, H-1,2), 7.62–7.60 (m, 1H, H-3), 7.00 (d, 2H, J=8.2 Hz, H-arom), 6.5 (d, 2H, J=8.2 Hz, H-aromatic), 5.19 (d, 1H, J=3.4 Hz, H-1'), 4.89 (, 1H, H-7), 4.38 (s, 1H, 9-OH), 4.14 (q, 1H, J=6.5 Hz, H-5'), 3.98 (s, 3H, OMe), 3.81 (m, 1H, H-4'), 3.78 (s, 2H, H-aromatic), 2.96 (d, 1H, J=18.0 Hz, H=10), 2.88 (d, 1H, J=19.0 Hz, H-10), 2.57 (m, 1H, H-3'), 2.25 (s, 3H, 14-$CH_3$), 2.14 (dd, 1H, J=14.3 Hz, J=3.0 Hz, H-8), 2.07 (dd, 1H, J=14.3 Hz, J=5.0 Hz, H-8), 1.66 (ddd, 1H, J=14.2 Hz, J=13.0 Hz, J=3.5 Hz, H-2'a), 1.55 (dd, 1H, J=13.0 Hz, J=4.4 Hz, H-2'e) 1.15 (d, 3H, J=6.5 Hz, H-6').

EXAMPLE 2

Synthesis of Exemplary C-4'-Alkyl-Aromatic Ring Anthracyclines

General Procedures for Making Anthracycline Analogs with C-4'-Substituted Sugars.

A. Synthesis of 4'-O-benzylated anthracyclines

1. Procedure A: Coupling and Deacetylation.

In the one flask a mixture of aglycon (1 mmol), $HgBr_2$ (0.7 g), HgO (2.8 g) and molecular sieves 4 A°(1 g) in dichloromethane (50 ml) was prepared and stirred at room temperature. At the same time, in the second flask, a trimethylsilyl bromide (3 mmol) was added to the solution of 1-O-silylated 3-azido-sugar (2 mmol) in dichloromethane (8 mL). Such reaction mixture was stirred at RT and its progress was monitored by TLC. (Toluene/acetone=8:1). After disappearance of starting sugar, solvent was removed under diminished pressure. Then hexanes (10 mL) were added to the residue and the mixture was evaporated. Such addition and removal of hexanes were repeated three times. Subsequently, the resulting dry residue was dissolved in the dichloromethane (10 mL). This solution was added in three portions to the first flask containing earlier prepared solution of aglycone and mercuric salts. The final reaction mixture was stirred at RT for 10 min. (progress of the reaction was monitored by TLC), then it was diluted with dichloromethane (50 mL), and filtered through Celite. Filtrate was washed with 10% water soln. of KI, then twice with water, and it was dried over $Na_2SO_4$. The crude product was purified by column chromatography and subsequently deacetylated in the mixture of methylene chloride and methanol (2:1, v/v) (50 mL), using solid potassium carbonate (2 g). The reaction mixture was stirred at RT until all substrate disappeared. (progress of the reaction was monitored by TLC). The mixture was diluted with dichloromethane (100 mL), then 1N water solution of HCl (15 mL), and water (50 mL) were added. The layers were separated. The organic layer was washed with water until neutral, then with brine, and it was dried over $Na_2SO_4$. The product was purified by column chromatography.

2. Procedure B: Reduction and Desilylation.

The coupling product containing azido group at the C-3' position (1 mmol) was dissolved in THF (8 mL). Triphenyl phosphine (2 mmol) was added to this solution, and reaction mixture was stirred at room temperature overnight. Progress of the reaction was monitored by TLC until disappearance of substrate. Then the reaction mixture was diluted with chloroform (50 mL) and 2N $NH_3$ in methanol (2 mL) was added to this solution. Reaction mixture was stirred for 1 h, then the solution was washed with water until neutral, then with brine, and dried over $Na_4SO_4$. Obtained crude product was purified by column chromatography. Anthracycline antibiotic with hydroxyl protected at 14 (1 mmol) was dissolved in THF (10 mL), then 1N HCl (15 mL) was added and the mixture was stirred at room temperature until all substrate disappeared as judge by TLC. The mixture was diluted with chloroform (20 mL). The layers were separated and the water solution was washed with chloroform until organic layer was colorless, and then saturated solution of $NaHCO_3$ was added to adjust pH to 8–9. Basic solution was extracted with chloroform contained 5% of methanol. Combined extracts were washed with brine and dried over dry $Na_2SO_4$. The solvent was removed under diminished pressure and dry product was dissolved in methanol (4 mL). IN solution of HCl in methanol (1.5 mL) followed by diethyl ether were added to this solution. Obtained solid hydrochloride was filtered off and washed with diethyl ether to remove excess of acid. When the filtrate was neutral, solid hydrochloride was precipitated from methanol/diethyl ether to give analytically pure product.

Figure 36:
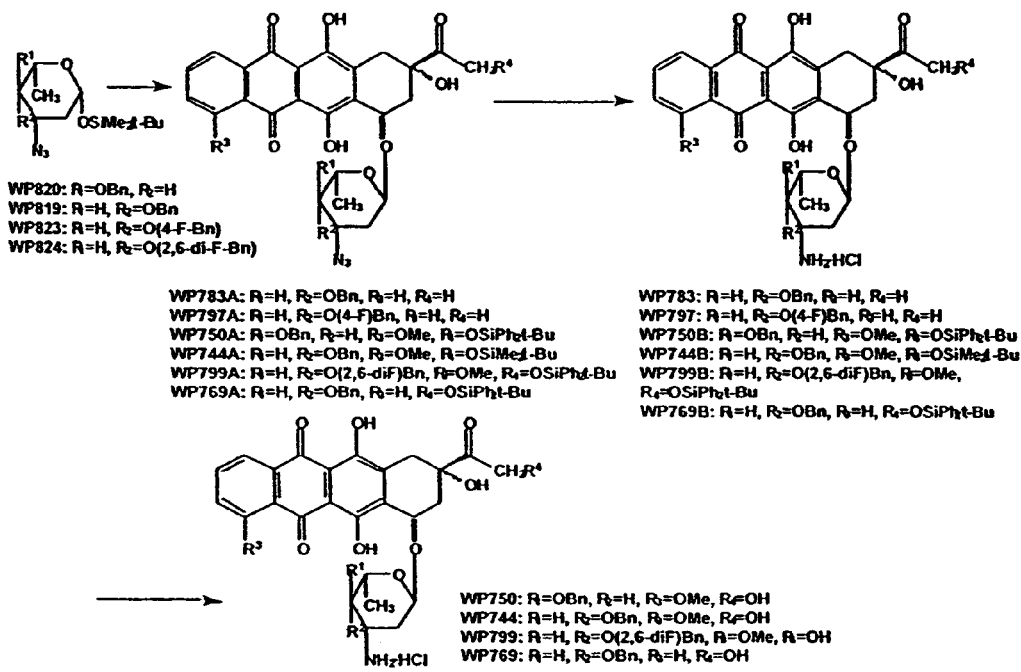
Figure 37:
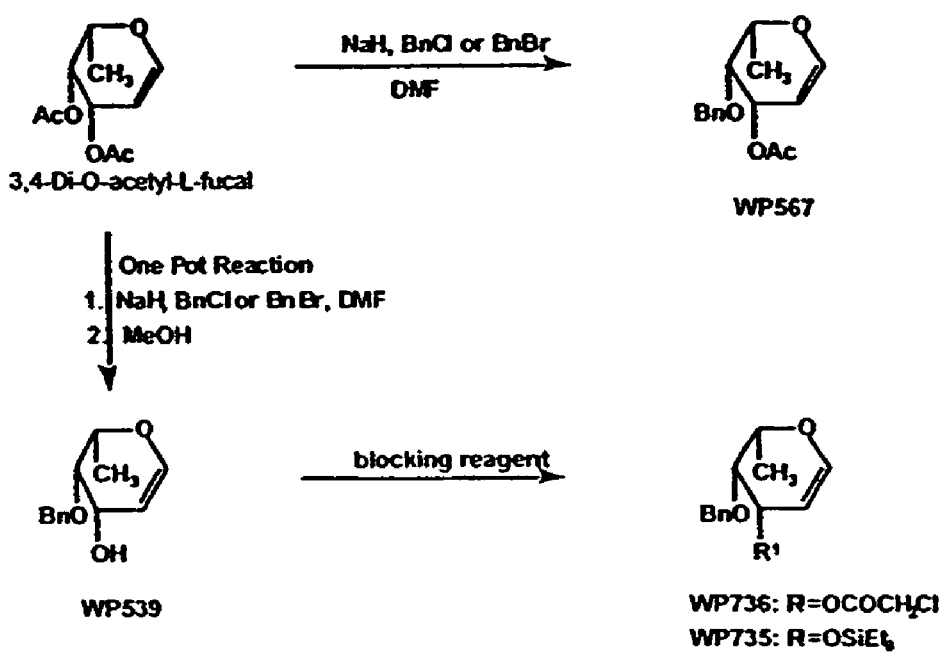

(i) WP 750A FIG. 36

3'-Deamino-3'-azido-4'-O-benzyl-14-O-tert-butyldiphenylsilyl-4'-epi doxorubicin.

Product was obtained according to the A. Yield 85%.

nmr($CDCl_3$) δ: 14.00, 13.19 (2s, 1H each, 6-OH, 11-OH), 8.02 (dd, 1H, J=8.47 Hz, J=0.98 Hz, H-1), 7.77 (dd, 1H, J=J=8.39 Hz, H-2), 7.70–7.76 (m, 4H), 7,45–7.30 (m, 12H, H-3), 5.39 (d, 1H, J=3.72 Hz, H-1'), 5.17 (bs, 1H, H-7), 4.89 (s, 2H, 14-$CH_2$), 4.81 (d, 1H, J=10.60 Hz, $CH_2$Ph), 4.60 (d, 1H, J=10.60 Hz, CH₂Ph), 4.16 (s, 1H, 9-OH), 4.07 (s, 3H, OMe), 3.71 (dq, 1H, J=9.4 Hz, J=6.2 Hz, H-5'), 3.56 (ddd, 1H, J=12.53 Hz, J=9.38 Hz, J=4.91 Hz, H 3'), 2.97 (dd, 1H, J=J=9.4 Hz, H4'), 2.97 (dd, 1H, J=18.94 Hz, J=1.24 Hz, H-10), 2.76 (d, 1H, J=18.94 Hz, H-10), 2.1–2.0 (m, 3H, H-8a,e, and H-2'e), 1.64 (ddd, 1H, J=13.28 Hz, J=13.28 Hz, J=4.07 Hz, H-2'a), 1.18 (d, 3H, J=6.2 Hz, H-6'), 1.12 (s, 9H, t-Bu).

(ii) WP 750 FIG. 21

4'-O-Benzyl-4'epi-doxorubicin

3'-Deamino-3'-azido-4'-O-benzyl-14-O-tert butyldiphenylsilyl-doxorubicin.

Product was obtained according to the Procedure (A), yield 90%.

nmr(CDCl3) δ: 13.90, 13.18 (2s, 1H each, 6-OH, 11-H), 8.01 (dd, 1H, J=7.49 Hz, J=0.9 Hz, H-1), 7.76 (dd, 1H, J=J=8.11 Hz, H-2), 7.72–7.69 (m, 4H), 7.47–7.33 (m, 12H, H-3 and H-aromatic), 5.49 (d, 1H, J=3.26 Hz, H-1'), 5.16 (, 1H, H-7), 4.83 (ABq, 2H, 14-CH2), 4.83 (d, 1H, J=11.14 Hz, CH2Ph), 4.57 (d, 1H, J=11.28 Hz, CH2Ph), 4.27 (s, 1H, 9-OH), 4.05 (s, 3H, OMe), 3.75 (q, 1H J=6.4 Hz, H-5'), 3.42–3.36 (m, 2H, H4', H-3), 3.00 (d, 1H, J=19.09 Hz, H-10), 2.80 (d, 1H, J=19.03 Hz, H-10), 2.17 (ddd, 1H, J=J=13.06 Hz, J=3.86 Hz, H-2'a), 2.1–1.95 (m, 2H, H-8a,e), 1.81(dd, 1H, J=13.06 Hz, J=3.81 Hz, H-2'e), 1.09 (s, 9H, t-Bu), 0.975 (d, 3H, J=6.4 Hz, H-6').

(iii) WP 744 FIG. 22

4'-O-Benzyl-doxorubicin

Product was obtained according to the procedure B., yield 40 n.m.r (DMSO) δ: 14.00, 13.22 (2s, 1H each, 6-OH, 11-OH), 8.15 (, 2H, NH2), 7.91–7.89 (m, 2H, H-1,2), 7.65–7.63 (m, 2H, H-3), 7.47–3.30 (m, 5H, H-aromatic), 5.45 (s, 1H, 14-OH), 5.40 (d, 1H, J=2.48 Hz, H-1'), 4.9 (, 1H, H-7), 4.85 (, 1H, 9-OH), 4.79 (d, 1H, J=11.13 Hz, Ch2Ph), 4.57 (s, 2H, 14-CH2), 4.56 (d, 1H, J=11.13 Hz, Ch2Ph), 4.23 (q, 1H, J=6.51 Hz, H-5'), 3.97 (s, 3H, OMe), 3.72 (, 1H, H-4'), 3.52–3.45 (m, 1H, H-3'), 2.97 (d, 1H, J=18.24 Hz, H-10), 2.85 (d, 1H, J=18.24 Hz, H-10), 2.14–2.05 (m, 2H, H-8), 1.87 (ddd, 1H, J=12.63 Hz, J=12.63 Hz, J=3.5 Hz, H-2'a), 1.71 (dd, 1H, J=12.63 Hz, J=4.38 Hz, H-2'e), 1.12 (d, 3H, J=6.48 Hz, H-6').

(iv) WP 783 FIG. 20

4'-O-Benzyl-4-demethoxydaunorubicin

The mixture of aglycone (1 mmol) HgBr2 (0.7 g), HgO (2.8 g) and molecular sieves 4 Å (1 g) in methylene chloride (50 mL) was prepared and stirred at room temperature. Trimethylsilyl bromide (3 mmol) was added to the solution of sugar (2 mmol) in dichlorometahne (8 mL). The obtained mixture was stirred at room temp., progress of the reaction was monitored by TLC (Toluene/acetone=8:1), until all substrate disappeared from reaction mixture, the solvent was removed under diminished pressure. Hexanes (10 mL) were added to the residue. Solvent was removed again, and the second portion of hexanes was added and then removed from the mixture. The addition and removal of hexanes was repeated three times then dry residue was dissolved in dichloromethane (10 mL). Obtained solution was added in three portions to the earlier prepared solution of aglycone and mercuric salts. The mixture was stirred at room temperature for 10 min. (reaction was controlled by TLC, then it was diluted with methylene chloride (50 mL), and filtered through Celite. Filtrate was washed with 10% water soln. of KI, then twice with water, and it was dried over Na2SO4. The crude product was purified by column chromatography (Eluent: toluene, toluene:acetone=100:1, 98:2). Product contained azido group in position 3' (1 mmol) was dissolved in THF (8 mL). Triphenyl phosphine (2 mmol) was added to this solution, and obtained mixture was stirred at room temperature overnight. Progress of the reaction was controlled by TLC. The reaction mixture was then diluted with chloroform, then 2N NH3 in methanol (2 mL) was added to this solution. Everything was stirred together for 1 hr, then the solution was washed with water until neutral, then with brine, and dried over Na2SO4. Crude product was purified by column chromatography (eluent:chloroform, chloroform: methanol=98:2, 95:5). Pure free amine was dissolved in methanol (4 mL), 1N solution of HCl in methanol (1.5 mL) followed by diethyl ether were added to this solution. Obtained solid hydrochloride was filtered off and washed with diethyl ether to remove excess of acid. When the filtrate was neutral, solid hydrochloride was precipitated from methanol/diethyl ether, gave analytically pure product. (Yield 40%).

1H n.m.r (CDCl3) δ: 8.35–8.33 (m, 2H, H-1,4), 7.85–7.80 (m, 2H, H-2,3), 7.42–7.29 (m, 5H, aromatic), 5.50 (d, 1H, J=3.55 Hz, H-1'), 5.28 (, 1H, H-7), 4.82 (d, 1H, J=11.52 Hz, aromatic), 4.76 (, 2H, NH2), 4.67 (d, 1H, J=11.51 Hz, aromatic), 4.10 (q, 1H, J=6.58 Hz, H-5'), 3.44 (, 1H, H-4'), 3.24 (dd, 1H, J=19.0 Hz, J=1.59 Hz, H-10), 3.05–2.95 (m, 1H, H-3'), 3.00 (d, 1H, J=19.0 Hz, H-10), 2.34 (d, 1H, J=14.77 Hz, H-8), 2.07 (dd, 1H, J=14.74 Hz, J=4.0 Hz, H-8), 1.85 (ddd, 1H, J=J=13.01 Hz, J=3.1 Hz, H-2'a), 1.70 (dd, 1H, J=13.09 Hz, J=4.53 Hz), 1.32 (d, 3H, J=6.57 Hz, H-6').

(v) WP 799 FIG. 17

4'-(2,6-difluoro-benzyloxy)-doxorubicine

Product was obtained according to the procedure A and B, yield 45% 1H n.m.r (CDCl3) δ: 7.9 (d, 1H, J=7.45 Hz, H-1), 7.72 (dd, 1H, J=7.9 Hz, J=7.9 Hz, H-2), 7.23 (d, 1H, J=7.8 Hz, H-3), 7.28–7.24 (m, 2H, aromatic), 6.89–6.86 (m, 2H, 2,6 aromatic) 5,44 (d, 1H, J=2.5 Hz, H-1'), 5.26 (, 1H, H-7), 4.76 (ABq, 2H, aromatic), 4.71 (s, 4H, aromatic and 9-OH) 4.10–3.98 (m, 1H, H-5'), 4.02 (s, 3H, OMe) 3.42 (, 1H, H-4'), 3.20 (d, 1H, J=19 Hz, H-10), 2.97 (d, 1H, J=19 Hz, H-10), 3.01–2.90 (m, 1H, H-3'), 2.27 (d, 1H, J=14.8 Hz, H-8), 2.07 (dd, 1H, J=14 Hz, J=3.7 Hz, H-8), 1.75–1.64 (m, 2H, H-2'a, H-2'e), 1.29 (d, 3H, J=6.5 Hz, H-6').

(vi) WP 797 FIG. 18

4'-(4-Fluoro-benzyloxy)-4-demethoxydaunorubicine

Product was obtained according to the procedure A and B, yield 60% 1H n.m.r (CDCl3) δ: 8.3–8.27 (m, 2H H-1, H4), 7.81–7.76 (m, 2H, H-2.3), 7.36–7.29 (m, 2H, 4F-Ph-CH2), 7.02–6.96 (m, 2H, 4F-Ph-CH2), 5.46 (d, 1H, J=3.5 Hz, H-1'), 5.24 (, 1H, H-7), 4.66 (ABq, 2H, 4F-Ph-CH2), 4.07 (q, 1H, J=6.59 Hz, H-5'), 3.39 (, 1H, H-4'), 3.20 (dd, 1H, J=19 Hz, J=1.9 Hz, H-10), 2.95 (d, 1H, J=19 Hz, H-10), 3.0–2.9 (m, 1H, H-3'), 2.37 (s, 3H, OMe), 2.30 (d, 1H, J=14 Hz, H-8), 2.03 (dd, 1H, J=14 Hz, J=4.2 Hz, H-8), 1.88 (ddd, 1H, J=13 Hz, J=13 Hz, J=3.93 Hz, H-2'a), 1.67 (dd, 1H, J=13 Hz, J=4.6 Hz, H-2'e), 1.26 (d, 3H, J=6.6 Hz, H6').

B. Synthesis of 3-azido-2,3,6-trideoxyhexopyranoses (3-azido-daunosamine and 3 azidoacosamine), sugars used in the synthesis of 4'-O-benzylated analogs of 3' amino-anthracyclines.

Figure 40:
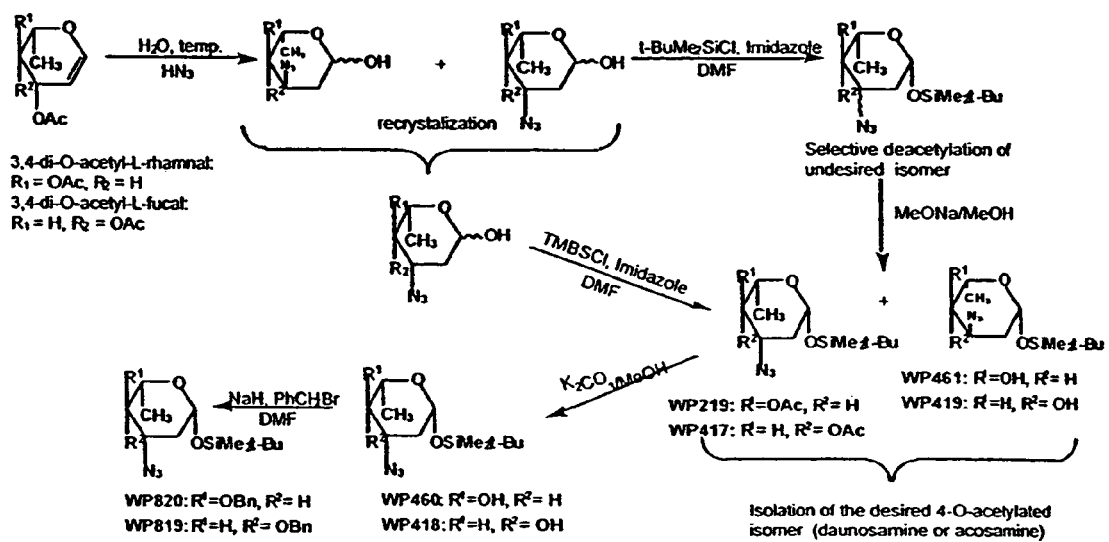

(vii) WP 219 FIG. 40

4-O-acetyl-3-azido-1-O-t-butyldimethylsilyl-2,3,6-trideoxy-b-L-arabino hexapyranose The mixture of 3,4-di-O-acetyl-L-rhaninal (1 mol) and water (2700 mL) was heated to 70° C., and it was stirred at this temperature until substrate is hydrolyzed (TLC). After substrate disappearance the mixture was cooled down to 0° C., then sodium azide (2.2 mol) followed by acetic acid (85 mL) were added to the mixture, and it was stirred at 0° C.

for 2 hr. Second portion of sodium azide (2.2 mol) and acetic acid (85 mL), and methylene chloride (1500 mL) were added to the reaction mixture, and it was stirred at room temperature overnight. The organic layer was separated, the water layer was extracted with dichloromethane (3×500 mL). Combined organic solutions were washed with water until neutral, then dried over Na2SO4. The drying agent and solvent were removed, and obtained product, light yellow oil was dried, gave crystals (0.9 mol). Obtained mixture of azides was dissolved in N,N dimethylformamide (300 ml), then imidazole (256 g), and tertbutyldimetylsilyl chloride (185 g) were added. The mixture was stirred at room temperature overnight, then it was diluted with water (600 mL) and extracted with hexanes (4×500 mL). The combined organic extracts were washed with water until neutral, then with brine, and it was dried over Na2SO4. The drying agent and solvent were removed and crude product—light yellow oil was dried with vacuum pump overnight. Product after silylation was dissolved in methanol (1400 mL), and cooled down to 0° C. then sodium methanolate (1M solution in methanol) (14 ml) was added. The reaction mixture was stirred at 0° C. for 3 hr., then 1 N water solution of HCl (14 ml) was added. The mixture was diluted with water (1400 mL), and extracted with hexanes (3×500 mL), then with dichloromethane (3×500 mL). The hexanes extracts were combined and washed with water until neutral, then with brine, and it was dried over Na2SO4. Crude product was purified by column chromatography, using as an eluent: hexanes, hexanes: ethyl acetate=98:2, gave colorless oil 4-O-acetyl-3-azido-1-O-t-butyldimethylsilyl-2,3,6-trideoxy-β-L-arabino hexopyranose (158 g; 0.48 mol). [a]D 1.46° (c=1.045, chloroform).

n.m.r (CDCl3) d: 4.82 (dd, 1H, J=9.3 Hz, J=1.9 Hz, H-1), 4.67 (t, 1H, J=J=9.8 Hz, H-4), 3.50 (ddd, 1H, J=4.9 Hz, J=12.8 Hz, J=9.8 Hz, H-3), 3.44 (qd, 1H, J=6.3 Hz, J=9.3 Hz, H-5), 2.20 (ddd, 1H, J=12.8 Hz, J=4.9 Hz, J=1.9 Hz, H-2e), 2.16 (s, 3H, OAc), 1.69 (ddd, 1H, J=12.8 Hz, J=12.8 Hz, J=9.3 Hz, H-2a), 1.21 (d, 3H, J=6.3 Hz, H-6), 0.90 (s, 9H, t-BuSi), 0.13, 0.11 (s, 3H, Me2Si).

Anal elem calc for C14H27N3O4Si: C: 51.04; H: 8.26; N: 12.75. Found: C: 51.3; H: 8.33; N: 12.47.

(viii) WP 460 FIG. 40

3-azido-1-O-t-butyldimethylsilyl-2,3,6-trideoxy-b-Larabino-hexapyranose

Obtained in previous step sugar (100 g) was dissolved in methanol (500 mL), then solid potassium carbonate (100 g) was added to this solution. The mixture was stirred at room temperature. After 0.5 hr reaction was completed, solid salts were filtered off. Organic solution was diluted with water (300 mL), and extracted with hexanes (3×300 mL), Combined extracts were washed with water until neutral, dried over sodium sulfate. The drying agent and solvents were removed gave pure product (white crystals), 82.8 g, yield 95%; [a]D+28.9° (c=1.3, chloroform). 1H n.m.r (CDCl3), d: 4.83 (dd, 1H, J=9.3 Hz, J=2.0 Hz, H-1), 3.42 (q, 1H, J=4.8 Hz, J=12.6 Hz, J=9.6 Hz, H-3), 3.35 (dq, 1H, J=6.1 Hz, J=9.0 Hz, H-5), 3.17(td, 1H, J=9.6 Hz, J=9.0 Hz, J=3.6 Hz, H-4), 2.30 (d,1H, J=3.6 Hz, 4-OH), 2.21 (ddd, 1H, J=12.6 Hz, J=4.8 Hz, J=2.0 Hz, H-2e), 1.68 (ddd, 1H, J=12.6 Hz, J=12.6 Hz, J=9.3 Hz, H-2a), 1.34 (d, 3H, J=6.1 Hz, H-6), 0.92 (s, 9H, t-Bu), 0.14, 0.13 (2s, 1H each, Me2Si).

Anal elem calc for C12H25N3O3Si: C: 50.14; H: 8.77; N: 14.62. Found: C: 50.20; H: 8.78; N: 14.54.

C. Alternative Method for Resolution of Mixture 3-azido-L-arabino- and 3-azido L-ribo-hexapyranoses.

3-Azido-2,3,6-trideoxy-L-arabino- and 3-azido-2,3,6-trideoxy-L-ribo hexapyranses obtained by hydrolysis of 3,4-do-O-acetyl-L-rhamnal and subsequent Michael addition of HN3, were separated by crystallization.

(ix) WP 417 FIG. 40

Synthesis of 3-azido-4-O-benzyl-2,3,6-trideoxy-L-lyxo-hexapyranoside t-Butyldimethylsilyl 3-azido-2,3,6-trideoxy-L-arabino-hexopyranose (WP460) (18.0 g, 62.7 mmol) was added to a solution of dry pyridine (38 ml) dichloromethane (1200 ml). The solution was purged with argon and cooled to −40° C. To this vigorous stirred mixture, solution of trifluoromethanesulfonic anhydride (38 ml, 63.4 g. 225 mmol) in methylene chloride (100 ml) was added dropwise through septum, during 1.5 h. The reaction mixture was allowed to warm up to the room temperature, then it was diluted with methylene chloride (300 ml) and washed with sodium acetate (10% aqueous solution) and phosphate buffer (pH 8) (2×200 ml). The solvent was evaporated twice with toluene (200 ml). The oily residue was dissolved in dry dimethylformamide (25 ml) and tetrabutylmmonium acetate (22.0 g, 71 mmol) was added to this solution. The mixture was stirred for 1 h at room temperature. After the complete disappearance of the triflate (TLC) the mixture was diluted with water (300 ml), and extracted with ethyl acetate (3×250 ml). Combined extracts were washed with 5% NaHCO3, and water until neutral. The organic layer was then dried over anhydrous sodium sulfate. Crude product was purified by column chromatography gave pure WP417 (15.5 g, 47.1 mmol). Yield: 75.1%; [a]D+5.3° (c=1.3, methylene chloride); 1H n.m.r (CDCl3) d: 5.06 (d, 1H, J=3.1 Hz, H-4), 4.78 (dd, 1H, J=8.4 Hz, J=2.8 Hz, H-1), 3.60 (q, 1H, J=6.44 Hz, H-5), 3.42 (ddd, 1H, J=12.1 Hz, J=5.3 Hz, J=3.2 Hz, H-3), 2.18 (s, 3H, OAc), 2.00–1.86 (m, 2H, H-2a, H-2e), 1.18 (d,3H, J=6.5 Hz, H-6), 0.91 (s, 9H, t-Bu), 0.14, 0.12 (2s, 3H each, Me2Si).

Anal Calc for: C14H27N3O4Si: H: 8.26; C: 51.04; N: 12.75. Found: H: 8.31; C: 51.22; N: 12.68.

(x) WP 418 FIG. 40 t-Butyldimethylsilyl 3-azido- -2,3,6-trideoxy-β-L-lyxo hexapyranose

Obtained in previous step sugar WP471 (15.5 g) was dissolved in methanol (100 ml), then solid potassium carbonate (15.5 g) was added to this solution. The mixture was stirred at room temperature. Progress of the reaction was monitored by T.L.C. After 0.5 hr reaction was completed, solid salts were filtered off. Organic solution was diluted with water (100 ml), and extracted with hexanes (3×200 ml), Combined extracts were washed with water until neutral and dried over sodium sulfate. The drying agent and solvents were removed gave pure product (white crystals), 13.25 g Yield: 98% mp 74–76° C., [a]D−4.1° (c=1.8, dichloromethane) 1H n.m.r (CDCl3) d: 4.74 (dd, 1H, J=9.1 Hz, J=2.4 Hz, H-1), 3.60 (dd, 1H, J=2.7 Hz, J=8.4 Hz, H-4), 3.50 (q, 1H, J=6.5 Hz, H-5), 3.30 (ddd, 1H, J=2.9 Hz, J=12.7 Hz, J=2.7 Hz, H-3), 2.03 (d, 1H, J=8.4 Hz, 4-OH), 1.99 (ddd, 1H, J=12.7 Hz, J=2.9 Hz, J=2.4 Hz, H-2e), 1.84 (td, 1H, J=12.7 Hz, J=12.7 Hz, J=9.1 Hz, H-2a), 1.29 (d, 3H, J=6.5 Hz, H-6), 0.90 (s, 9H, t-Bu), 0.13, 0.11 (s, 3H each, Me2Si).

Anal Calc for: C12H25N3O3Si: H: 8.77; C: 50.14; N: 14.62. Found: H: 8.80; C: 50.11; N: 14.52.

(xi) WP 819 FIG. 26

1-O-t-butyldimethylsilyl-3-Azido-4-O-benzylo-2,3,6-trideoxy-β-L-lyxo hexapyranose Sodium hydride (1 g of 60% suspension in mineral oil) was added to a cooled to 0° C. solution of WP 418(3.9 g, 13.5 mmol) in dry N,N dimethylformamide (40 ml). The reaction mixture was stirred for 15 min, then solution of benzyl bromide (2.97 ml, 4.27 g, 25 mmol) was added. The stirring continued for 0.5 h at 0° C., then mixture was allowed to warn up to room temperature. The reaction mixture was poured into the ice/water and extracted with ethyl acetate (3×100 ml). The combined extracts were washed with water, then with saturated solution of sodium bicarbonate and dried over magnesium sulfate. The pure product (3.145 g, 8.34 mmol) was separated by column chromatography. Yield: 61.8%. 1H n.m.r (CDCl3) d: 7.4–7.2 (m, 5H, H-aromatic), 4.84 (d, 1H, J=11.4 Hz, H-aromatic), 4.70 (dd, 1H; J=9 Hz, J=2.19 Hz, H-1), 4.61 (d, 1H, J=11.4 Hz, Ch2Ph), 3.39 (q, 1H, J=6.1 Hz, H-5), 3.33 (d, 1H, J=2.67 Hz, H4), 3.25 (ddd, 1H, J=4.46 Hz, J=12.8 Hz, J=2.67 Hz, H-3), 2.03 (ddd, 1H, J 12.3 Hz, J=12.8 Hz, J=9 Hz, H-2a), 1.90 (ddd, 1H, J=12.3 Hz, J=4.46 Hz, J=2.19 Hz, H-2e), 1.15 (d, 3H, J=6.1 Hz, H-6), 0.90 (s, 9H, t-Bu), 0.13, 0.11 (s, 3H each, Me2Si).

D. Direct Synthesis of 3-azido-daunosamine.

(xii) WP 417 FIG. 40

4-O-acetyl-3-Azido-1-O-t-butyldimethylsilyl-2,3,6-trideoxy-β-L-lyxo hexapyranose The mixture of 3,4-di-O-acetyl-fucal (1 mol) and water (2700 mL) was heated to 80° C., and it was stirred at this temperature until all 3,4-di-O-acetyl-fucal hydrolysed (TLC). After all substrate disappeared from reaction mixture, the mixture was cooled down to 0° C., then sodium azide (2.2 mol) followed by acetic acid (85 mL) were added to the mixture, and it was stirred at 0° C. for 2 hr. Second portion of sodium azide (2.2 mol) and acetic acid (85 mL), and dichloromethane (1500 mL) were added to the reaction mixture, and it was stirred at room temperature overnight. The organic layer was separated, the water layer was extracted with dichloromethane (3×500 mL). Combined organic solutions were washed with water until neutral, then dried over Na2SO4. The drying agent and solvent were removed, and obtained product mixture, a light yellow oil was dried, to gave crystals (0.89 mol). Obtained mixture of azides was dissolved in dimethylformamide (300 mL), then imidazole (256 g), and tert butyldimetylsilyl chloride (185 g) were added. The mixture was stirred at room temperature overnight, then it was diluted with water (600 mL) and extracted with hexanes (4×500 mL). The combined organic extracts were washed with water until neutral, then with brine, and it was dried over Na2SO4. The drying agent and solvent were removed and crude product, light yellow oil was dried overnight Product after silylation was dissolved in methanol (1400 mL), and cooled down to 0° C. then sodium methanolate (1 M solution in methanol) (14 mL) was added. The reaction mixture was stirred at 0° C. for 3 hr., then 1 N water solution of HCl (14 mL) was added. The mixture was diluted with water (1400 mL), and extracted with hexanes (3×500 mL), then with methylene chloride (3×500 mL). The hexanes extracts were combined and washed with water until neutral, then with brine, and it was dried over Na2SO4. Crude product was purified by column chromatography, using hexanes, hexanes: ethyl acetate=98:2 as eluent, gave analytically pure product (48.5 g; 0.168 mol); [a]D+5.3° (c=1.3, chloroform) 1H n.m.r (CDCl3) d: 5.06 (d, 1H, J=3.1 Hz, H-4), 4.78 (dd, 1H, J=8.4 Hz, J=2.8 Hz, H-1), 3.60 (q, 1H, J=6.44 Hz, H-5), 3.42 (ddd, 1H, J=12.1 Hz, J=5.3 Hz, J=3.2 Hz, H-3), 2.18 (s, 3H, OAc), 2.00–1.86 (m, 2H, H 2a, H-2e), 1.18 (d,3H, J=6.5 Hz, H-6), 0.91 (s, 9H, t-Bu), 0.14, 0.12 (2s, 3H each, Me2Si).

Anal elem calc for: C14H27N3O4Si: C: 51.04; H: 8.26; N: 12.75. Found: C: 51.22; H: 8.31; N: 12.68.

E. 4'-O-benzylated-3'-hydroxy-doxorubicin Analogs:

(xiii) WP 568 FIG. 35

Synthesis of 3-Oacetyl-4-Obenzyl-3-deamino-14-Ot-butyldiphenylsilyl-doxorubicin.

A mixture of 14-O-t-butyldiphenylsilyl-adriamycinone (0.84 g, 1.29 mmol), 3-O-acetyl-4-O-benzyl-L-fucal (0.84 g, 3.2 mmol), triphenylphosphine hydrobromide (0.055 g, 0.16 mmol) in dichloromethane (18 mL) was stirred for 48 hr. During this time additional portion of 3-O-acetyl-4-O-benzyl-L-fucal (0.175 g, 0.7 mmol) was added and stirred for 24 hours. The reaction mixture was diluted with dichloromethane (200 mL), washed with water and dried with anhydrous Na2SO4. The product was purified by chromatography on silicagel column using dichloromethane:acetone (95:5 vol.) to give 3-O-acetyl-4-O-benzyl-3-deamino-14-O-t-butyldiphenylsilyl-doxorubicin (WP 568) (1.0 g, 1.09 mmol). Yield: 84%. [a]D 116.84o (c=0.0354, chloroform:methanol 1:1). 1H n.m.r (CDCl3) d: 13.94 (s, 1H, OH-6), 13.24 (s, 1H, OH-1), 8.1 (d, 1H, J=7.8 Hz, H-1), 7.68–7.85 (m, 5H, J=8.1 Hz, from silyl, H-2), 7.5–7.2 (m, 12H, J=7.3 Hz, from silyl, Ch2Ph, H-3), 5.49 (d, 1H, J=3.9 Hz, H-1), 5.19 (bs, 1H, H-7), 5.0–4.78 (m, 3H, J=19.8 Hz, H-14, H-3), 4.7 (d, 1H, J=11.6 Hz, Ch2Ph), 4.59 (d, 1H, J=11.8 Hz, Ch2Ph), 4.29 (s, 1H, OH-9), 4.07 (s, 3H, CH3O), 3.90 (q, 1H, J=6.5 Hz, H-5), 3.60 (bs, 1H, H4), 3.02 (d, 1H, J=19.3 Hz, H-10eq), 2.85 (d, 1H, J=19.1 Hz, H-10ax), 2.3–1.95 (m, 3H, H-8, H-2a), 1.93 (s, 3H, CH3CO), 1.8 (dd, 1H, J=3.8 Hz, J=12.7 Hz, H-2e), 1.43 (s, 9H, tBu), 1.07 (d, 3H, J=6.5 Hz, H-6).

(xiv) WP 569 FIG. 35

Synthesis of 4-Obenzyl-3-deamino-3-hydroxy-14-O-t-butyldiphenylsilyl-doxorubicin.

3-O-Acetyl-4-O-benzyl-3-deamino-14-O-t-butyldiphenylsilyl-doxorubicin (WP 568) (1.0 g, 1.09 mmol) was dissolved in mixture of tetrahydrofuran (20 mL) and methanol (80 mL), and then anhydrous potassium carbonate (1.0 g, 7.2 mmol) was added. The reaction mixture was stirred vigorously at room temperature for 2 h, until substrate disappeared. Then reaction mixture was diluted with dichloromethane (300 mL) and poured into 0.05 N HCl (100 mL), extracted with dichloromethane, washed with water, dried with anhydrous Na2SO4. The solvent was evaporated and the residue was chromatographed using dichloromethane: acetone (9:1 vol.) to give 4-O-benzyl-3-deamino-3-hydroxy-14-O-t-butyldiphenylsilyl-doxorubicin (WP 569) (0.6 g, 0.687 mmol). Yield: 63%. [a]D 52.94o (c=0.022, chloroform:methanol 1:1). 1H n.m.r (CDCl3) d: 13.93 (s, 1H, OH-6), 13.23 (bs, 1H, OH-11), 8.02 (d, 1H, J=7.6 Hz, H-1), 7.82–7.67 (m, 5H, from silyl, J=8.2 Hz, H-2), 7.45–7.25 (m, 12H, J=8.3 Hz, from silyl, Ch2Ph, H-3), 5.47 (d, 1H, J=3 Hz, H-1), 5.19 (bs, 1H, H-7), 4.95 (d, 1H, J=19.8 Hz, H-14), 4.84 (d, 1H, J=19.8 Hz, H-14), 4.80 (d, 1H, J=11.6 Hz, Ch2Ph), 4.64 (d, 1H, J=11.6 Hz, Ch2Ph), 4.43 (s, 1H, OH-9), 4.07 (s, 3H, CH3O), 3.92 (q, 1H, J=6.5 Hz, H-5), 3.70 (bs, 1H, H-3), 3.45 (d, 1H, J=2.3 Hz, H-4), 3.0 (d, 1H, J=19 Hz, H-10eq), 2.83 (d, 1H, J=19 Hz, H-10ax), 2.35 (s, 1H, OH), 2.12–195 (m, 2H, H-8), 1.92–1.7 (m, J=3.8 Hz, H-2) 1.13 (s, 12H, tBu), 1.11 (s, 3H, H-6).

(xv) Synthesis of 4-Obenzyl-3-Deamino-3-Hydroxy-Doxornbicin—WP 727 FIG. 23

4-O-Benzyl-3-deamino-3-hydroxy-14-O-t-butyldiphenylsilyl-doxorubicin (WP 569) (0.6 g, 0.687 mmol) was dissolved in THF (33 mL), and a reagent (25 mL)/made from THF (24 mL), dichloromethane (12 mL), pyridine (0.66 mL), 1.0M Bu4NF (0.6 mL)/was added, and stirred vigorously until substrate disappear. Then the reaction mixture was poured into solution containing ice (50 g), 0.1 N HCl (100 mL), dichloromethane (100 mL). Organic layer was separated and water layer was extracted with dichloromethane (3×50 mL). The combined organic layers were washed with water, dried with anhydrous Na2SO4, evaporated, and chromatographed on silicagel column using dichloromethane:acetone (7:3 vol.) to give pure product 4-O-benzyl-3-deamino-3-hydroxy-doxorubicin (WP 570) (0.34 g, 0.536 mmol). Yield: 78%. [a]D 101.00o (c=0.029, chloroform:methanol 1:1). 1H n.m.r (CDCl3) d: 13.93 (s, 1H, OH-6), 13.22 (s, 1H, OH-11), 8.02 (d, 1H, J=8 Hz, H-1), 7.77 (t, 1H, J=8 Hz, H-2), 7.38 (m, 6H, H-aromatic, H-3), 5.55 (d, 1H, J=3.2 Hz, H-1), 5.26 (s, 1H, H-7), 4.83 (dd, 1H, J=11.8 Hz, H-14), 4.7–4.65 (m, 4H, J=2.75 Hz, H-14, H-aromatic, OH-9), 4.07 (s, 3H, CH3O), 4.03 (q, 1H, J=6.6 Hz, H-5), 3.9–3.78 (m, 1H, H-3), 3.57 (d, 1H, J=2.52 Hz, H-4), 3.25 (dd, 2H, J=1.5 Hz, J=18.7 Hz, H-10eq), 3.01 (d, bs, 3H, J=18.8 Hz, H-10ax, OH-3), 2.32 (bd, 1H, J8e–8a =14.8 Hz, H-8eq), 2.13 (dd, 1H, J=3.9 Hz, J8a–8e=14.7 Hz, H-8ax), 1.95 (dt, 1H, J=4 Hz, J=12.8 Hz, H-2a), 1.84 (dd, 1H, J=4.8 Hz, J=12.8 Hz, H-2e ), 1.33 (d, 3H, J=6.5 Hz, H-6).

Figure 38:
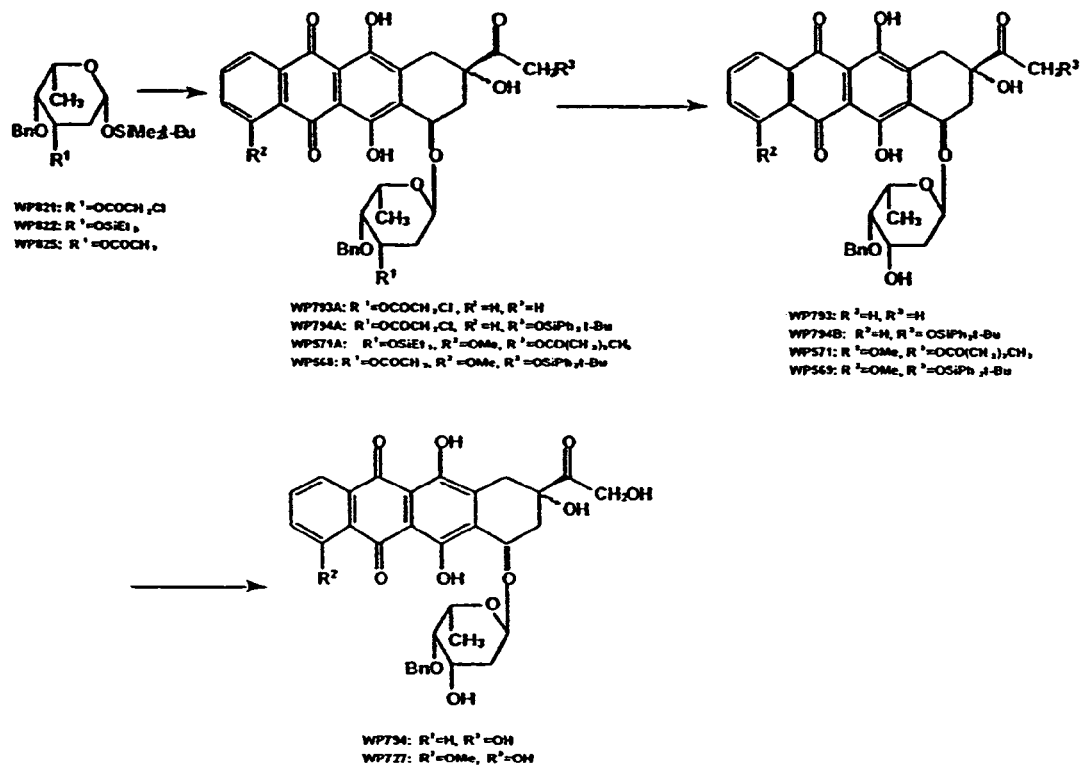

(xvi) WP 571 FIG. 38

Synthesis of 4-Obenzyl-3-deamino-3-Otriethylsilyl-14-Opentanoyl-doxorubicin.

A mixture of 14-O-pentanoyl-adriamycinone (0.6 g, 1.2 mmol), 4-O-benzyl-3-O-triethylsilyl-L-fucal (1.1 g, 3.3 mmol), sieves 4 (0.5 g), TPHB (0.06 g, 0.18 mmol) in dichloromethane (20 mL) was stirred overnight at room temperature. Then the reaction mixture was diluted with dichloromethane (100 mL) and washed with water, dried with anhydrous Na2SO4; the solvent was evaporated, and the residue was chromatographed on silicagel columusing dichloromethane:acetone (98:2 vol.) to give 4-O-benzyl-3-deamino-3-O-triethylsilyl-14-O-pentanoyl-doxorubicin (0.89 g, 1.07 mmol). Yield: 89%. 1H n.m.r (CDCl3) d: 13.94 (s, 1H, OH-6), 13.25 (s, 1H, OH-11), 8.03 (d, 1H, J=7.8 Hz, H-1), 7.77 (t, 1H, J=8 Hz, H-2), 7.43–7.26 (m, 6H, J=7.2 Hz, H-aromatic, H-3), 5.55 (d, 1H, J=3.7 Hz, H-1), 5.31 (bs, 1H, H-7), 5.32 (d, 1H, J=18.2 Hz, H-14), 5.12 (d, 1H, J=18.2 Hz, H-14), 4.98 (d, 1H, J=12.6 Hz, Ch2Ph), 4.92 (s,1H, OH-9), 4.67 (d, 1H, J=12.7 Hz, Ch2Ph), 4.08 (s, 3H, CH3O), 4.02–3.90 (q, m, 2H, J5=6.5 Hz, H-5, H-3), 3.45 (bs, 1H, H-4), 3.28 (d, 1H, J=19 Hz, H-10eq), 3.03 (d, 1H, J=19 Hz, H-10ax), 2.50–2.38 (m, 4H, J=7.4 Hz, CH2 from pentanoyl, H-8), 2.22 (dt, 1H, J=3.1 Hz, J=12.7 Hz, H-2a), 2.06 (dd, 1H, J=3.8 Hz, J=12.7 Hz, H-2e), 1.77–1.62 (m, 2H, J=7.4 Hz, CH2 from pentanoyl), 1.48–1.35 (m, 2H, J=7.5 Hz, CH2 from pentanoyl), 1.23 (d, 3H, J=6.5 Hz, H-6), 0.95 (t,t, 12H, J=7.8 Hz, CH3 from pentanoyl, (Et)3Si), 0.58 (q, 6H, J=8 Hz, (Et)3Si).

(xvii) WP 571 FIG. 38

Synthesis of 4-Obenzyl-3-Deamino-3-Hydroxy-14-Opentanoyl-Doxorubicin

4-O-Benzyl-3-deamino-3-O-triethylsilyl-14-O-pentanoyldoxorubicin (0.715 g, 0.86 mmol) was dissolved in THF (15 mL), and then 0.1 N HCl (10 mL) was added. Reaction mixture was stirred at room temperature for 1 h until substrate disappeared. Then the reaction mixture was diluted with water (30 mL); a precipitate was filtered, washed with water and dried at 100 C. under diminished pressure overnight to give pure 3-deamino-4-O-benzyl-3-O-hydroxy-14-O-pentanoyl-doxorubicin (WP 571) (0.56 g, 0.78 mmol). Yield: 91%. 1H n.m.r (CDCl3) d: 13.91 (s, 1H, OH-6), 13.18 (s, 1H, OH-11), 7.99 (d, 1H, J=7.7 Hz, H-1), 7.75 (t, 1H, J=8 Hz, H-2), 7.46–7.29 (m, 6H, H-aromatic, H-3), 5.54 (d, 1H, J=3.2 Hz, H-1), 5.32 (d, 1H, J=18.1 Hz, H-14), 5.25 (bs, 1H, H-7), 5.10 (d, 1H, J=18.2 Hz, H-14), 4.85 (d, 1H, J=11.7 Hz, Ch2Ph), 4.74 (s, 1H, OH-9), 4.69 (d, 1H, J=11.7 Hz, C2Ph), 4.12–4.00 (q, s, 4H, H-5, CH3O), 3.90–3.70 (m, 1H, H-3), 3.58 (d, 1H, J=2 Hz, H-4), 3.25 (d, 1H, J=18.7 Hz, H-10eq), 2.97 (d 1H, J=18.7 Hz, H-10ax), 2.52–2.38 (m, 3H, J=7.4 Hz, CH2 from pentanoyl, H-8), 2.08 (dd, 1H, J=3.8 Hz, J=14.9 Hz, H-8), 1.95 (dt, J=4 Hz, J=12.9 Hz, H-2a), 1.89–1.82 (dd, 1H, J=5 Hz, J=12.9 Hz, H-2e), 1.75 (d, 1H, J=9.4 Hz, OH-3), 1.75–1.65 (m, 2H, J=7.4 Hz, CH2 from pentanoyl), 1.48–1.3 (m, 2H, J=7.4 Hz, CH2 from pentanoyl), 1.36 (d, 3H, J=6.5 Hz, H-6), 0.95 (t, 3H, J=7.4 Hz, CH3 from pentanoyl).

EXAMPLE 3

Novel Method for the Synthesis of 4-O-Benzylated Sugars

Described herein is a method for the preparation of the 4-O-benzylated sugars, used as precursors in the synthesis of 4-O-benzylated-3-hydroxy-anthracyclines like WP727, WP571, WP794, or WP793. This is a novel method superior to other methods described earlier. A direct selective alkylation of acetylated glycals is used which gives almost exclusively products alkylated at C-4. The inventors approach is different from other known methods in the following ways: (1) a one step approach wherein a fully blocked compound is alkylated allowing for an easier and simpler synthesis versus the standard method of alkylating free hydroxyl groups, (2) because the process is selective the major products are 4-O-alkylated compounds. In this method, the first step of the reaction is a selective deblocking (deacylation) of the hydroxyl at C-4 followed by a rapid alkylation of this free hydroxyl group. In contrast, alkylation of unblocked (hydroxy compounds) glycals gives mixtures of mono-benzylated and dibenzylated products and 4-O-benzylated-glycals are obtained in lower yields.

Such 4-O-benzylated glycals can be used directly towards synthesis of the 4-O-benzylated anthracycline analogs described in the previous example, using electrophilic addition to glycals in the presence of triphenylphosphine hydrobromide (TPHB), for example the synthesis of WP727.

The inventors method works well not only for the 6-deoxy-glycals like fucal and rhamnal but to also for glycals like D-glucal or D-galactal having hydroxyl groups at C-3, 4, and 6 positions. Direct alkylation of 3,4,6-tri-O-acetylated-D-glucal or -D-galactal give 4-O-benzylated-glycals as a the main product. Therefore, this method is of general use.

More importantly, the inventors found that these reactions can be continued in the same vessel to the next step to synthesize 3-hydroxy-4-O-benzylated glycals. For this the other acetyl groups are removed by the addition of methanol to the reaction mixture. Methanol forms in situ sodium methoxide, which in turn deacetylates all hydroxyl groups. Described below are the experimental procedures and data for the 4-O-benzylated substrates which are either acetylated or bear free hydroxyl groups, and data for other 4-O-benzylated sugars to prove the general nature of the inventors approach.

This method can be used to synthesize 4-O-benzylated products and also other 4-O-alkylated products. The 4-O-benzylated glycals can then be used directly in the coupling reactions with proper aglycon -like daunomycinone or can be first transformed into 4-O-alkylated 1-O-silylated hex-opyranoses which can further be coupled using a variety of other coupling methods as for example in the synthesis of WP793 and WP794.

A. Synthesis of 4-O-Alkylated-Glycals: FIG. 39.

1. Examples of Selective Benzylation of Glycals at the C-4 Position (i) Selected procedure for 4-O-benzyl-L-rhamnal exemplifying general procedure. To a solution of NaH (2.5 g, 0.063 mmol) in DMF (30 mL) cooled to ?C 3,4-di-O-acetyl-L-rhamnal (6.5 g, 0.03 mmol) was added. The reaction mixture was stirred for 15 min, and benzyl, chloride (6 mL, 0.046 mmol) was added. Then the reaction was allowed to warm up to room temperature and stirred until TLC showed complete consumption of starting material. The reaction was cooled to 0° C. methanol (10 ml) was added, with continous stirring for 10 min. The reaction mixture was then poured into a solution containing 1 N HCl (10 mL), ice (20 g), and ethyl acetate (50 mL). The organic phase was separated and aqueous phase was extracted with ethyl acetate (3×50 mL). The combined organic solution was washed with water, dried with anhydrous Na2SO4, and concentrated to give an oily-solid product that was crystallized from dichloromethane/hexane.

(ii) 4-OBenzyl-L-rhamnal Yield: 73%, mp 110–110.5 C. [a]D −44.12o (c=1.05, ethyl acetate). 1H n.m.r (CDCl3) d: 7.6–7.0 (m, 5H, H-aromatic), 6.32 (dd, 1H, J=5.7 Hz, H-1), 4.90–4.72 (dd, 2H, J=11.8 Hz, Ch2Ph), 4.69 (dd, 1H, J1,2=5.7 Hz, J2,3=2 Hz, H-2), 4.34 (m, 1H, H-3), 3.97–3.85 (dq, 1H, J5,4=9.4 Hz, J5,6=6.3 Hz, H-5), 3.32–3.22 (dd, 1H, J4,5=9.4 Hz, H-4), 1.70 (d, 1H, J=5.8 Hz, OH), 1.40 (d, 3H, J6,5=6.3 Hz, H-6).

(iii) 4-OBenzyl-L-fucal Yield: 63%, mp 77.0–77.5 C. [a]D 13.3o (c=1.18, chloroform). 1H n.m.r (CDCl3) d: 7.55–7.30 (m, 5H, H-aromatic), 6.36 (dd, 1H, J1,2=6 Hz, J1,3=0.9 Hz, H-1), 4.8 (m, 2H, H-aromatic), 5.75–5.68 (m, 1H, H-2), 4.45–4.35 (m, 1H, H-3), 4.08 (q, 1H, J5,6=6.6 Hz, H-5), 3.68 (d, 1H, J=5.1 Hz, H-4), 2.23 (d, 1H, J=10 Hz, OH), 1.35 (d, 1H, J6,5=6.6 Hz, H-6).

(iv) 4-OBenzyl-D-glucal Yield: 72%, mp 98.5–100 C. [a]D 10.37o (c=1.4, chloroform). 1H n.m.r (CDCl3) d: 7.5–7.25 (m, 5H, H-aromatic), 6.37 (dd, 1H, J1,2=5.9 Hz, J1,3=1.1 Hz, H-1), 4.95–4.78 (dd, 2H, H-aromatic), 4.75 (dd, 1h, J2,1=5.9 Hz, J2,3=2.3 Hz, H-2), 4.41 (m, 1H, H-3), 4.02–3.82 (m, 3H, H-6, H-5), 3.65 (t, J=6.9 Hz, H4), 1.90 (d, J=12.7 Hz, 1H, OH).

(v) 4-O-Benzyl-D-galactal Yield: 55%, mp 98.5–99° C.

2. Selected Procedure for Preparation of 3-Oacetyl-4-Obenzyl-L-rhamnal Exmeplifying General Procedure.

To a solution of NaH (2.5 g, 0.063 mmol) in DMF (30 mL) cooled to 0 C. 3,4-di-O-acetyl-L-rhamnal was added (6.5 g, 0.03 mmol). The reaction was stirred for 15 min, and BnCl (6 ml, 0.046 mmol) was added. Then the reaction was allowed to warm up to room temperature and stirred vigorously until TLC showed complete consumption of starting material. After 1.5 h reaction mixture was poured into solution containing 1 N HCl (10 mL), ice (20 g), and ethyl acetate (50 mL). The organic phase was separated and aqueous phase was extracted with ethyl acetate (3×50 ml). The combined organic solution was washed with water, dried with anhydrous Na2SO4, and concentrated to give an oil that was purified by column chromatography on silicagel column using hexane:ethyl acetate 95:5 as eluents to give pure 3-O-acetyl-4-O-benzyl-L-rhamnal.

(vi) 3-OAcetyl-4-Obenzyl-L-rhamnal Yield: 50%, bp 200 C./0.04 mm Hg. [a]D 55.77o (c=1.15, ethyl acetate). 1H n.m.r (CDCl3) d: 7.42–7.25 (m, 5H, H-aromatic), 6.4 (d, 1H, J=6.5 Hz, H-1), 5.43–5.36 (m, 1H, H-3), 4.78 (dd, dd, 3H, J2,3=2.5 Hz, J2,1=5.8 Hz, J=11.5 Hz, Ch2Ph, H-2),4.1–4.0 (m, 1H, J5,4=8.4 Hz, J5,6=6.5 Hz, H-5), 3.57–3.49 (dd, 1H, J4,5=8.2 Hz, H-4), 2.02 (s, 3H, CH3CO), 1.38 (d, 3H, J6,5=6.7 Hz, H-6).

(vii) 4-OBenzyl-3,6di-Oacetyl-D-glucal Yield: 50%, mp 52–55.5 C. [a]D −7.34o (c=1.4, ethyl acetate). 1H n.m.r (CDCl3) d: 7.42–7.18 (m, 5H, H-aromatic), 6.42 (d, 1H, J=6.3 Hz, H-1), 5.43–5.38 (m, 1H, J=5.3 Hz, J=3.2 Hz, H-3), 4.83–4.78 (dd, 1H, J=5.9 Hz, J=3.1 Hz, H-2), 4.72 (d, 1H, J=11.6 Hz, Ch2Ph), 4.64 (d, 1H, J=11.6 Hz, Ch2Ph), 4.42–4.29 (m, 2H, H-6), 4.2–4.12 (m, 1H, H-5), 3.85–3.78 (dd, 1H, J4,5=8 Hz, H-4), 2.07 (s, 3H, CH3CO), 2.04 (s, 3H, CH3CO).

(viii) 4-OBenzyl-3,6-di-Oacetyl-D-galactal Yield: 59%. 1H n.m.r (CDCl3) d: 7.42–7.18 (m, 5H, H-aromatic), 6.4 (d, 1H, J=6.2 Hz, H-1), 5.53–5.4.(m, 1H, J=4.4 Hz, J=4 Hz, H-3), 4.85–4.77 (dd, 1H, J2,1=6.1 Hz, J2,3=4.3 Hz, H-2), 4.74 (d, 1H, J=11.8 Hz, Ch2Ph), 4.55 (d, 1H, J=11.9 Hz, Ch2Ph), 4.52–4.43 (dd, 1H, J=11.7 Hz, J=8.5 Hz, H-5), 4.34–4.2 (m, 2H, J=11.7 Hz, H-6), 3.99 (t, 1H, J4,3=4 Hz, H-4), 2.09 (s, 3H, CH3CO), 2.06 (s, 3H, CH3CO).

(ix) 3-OAcetyl-4-Obenzyl-L-fucal Yield: 58% bp 190 C/0.02 mm Hg. [a]D 61.4 (c=0.6, chloroform).

(x) 3OAcetyl-4-Obenzyl-Larabinal Yield: 59%.

(xi) 3-OAcetyl-4-Obenzyl-L-xylal Yield: 39%. 1H n.m.r (CDCl3) d: 7.4–7.25 (m, 5H, H-aromatic), 6.01 (d, 1H, J1,2=6.1 Hz, H-1), 5.9 (t, 1H, J2,1=6.3 Hz, H-2), 5.4–5.25 (m, 1H, H-3), 4.75–4.62 (dd, 2H, J=12.2 Hz, Ch2Ph, H-2), 4.15 (m, 1H, J5,5=11.6 Hz, H-5), 3.9 (m, 1H, J5,5=11.7 Hz, H-5), 3.65–3.57 (m, 1H, H-4), 2.02 (s, 3H, CH3CO).

3. General Procedure for Preparation of 3-O-silylated-4-O-benzyl-L-glycals.

4-O-Benzyl-L-fucal (1.5 g,10.4 mmol) was silylated with Et3SiCl (1.1 ml, 10.4 mmol) in presence of imidazole (1.1 g, 17 mmol) in DMF (3 mL). Reaction was finished after 2 h, then water (2 mL) was added, and stirring was continued for 5 min. Then the reaction mixture was extracted with ethyl ether (3×10 ml). The combined organic solution was washed with water, dried with anhydrous Na2SO4, and concentrated to give an oil that was distilled on Kugelrohr 150 C/0.03 mm Hg to give pure 4-O-benzyl-3-O-triethylsilyl-L-fucal (2.2 g, 6.6 mmol). Yield: 97%.

(xii) 4-Benzyl-3-O-t-butyldimethylsilyl-L-rhamnal. Yield: 98%.

EXAMPLE 4

Assessment of Anti-tumor Activity in Vitro

Compounds synthesized using the methods described above were tested using a standard MTT. assay (Green et al., 1984) against human carcinoma sensitive (KB) and multi drug-resistant (KBV1) cells and MCF-7 and MCF-7/VP-16 resistant cells characterized as having the MRP (multi-drug resistant associated protein) phenotype. The use of an MTT assay using these cells is recognized as an accepted assay for anti-tumor activity by those in the field.

Methods

In vitro Cytotoxicity against MCF-7, MCF-7/VP-16, and MCF-7/DOX cell lines. In vitro drug cytotoxicities against human breast carcinoma wild-type MCF-7 and MRP-resistant MCF-7NP-16 cells were assessed by using the MT reduction assay, as previously reported (Green et al., 1984). The MTT dye was obtained from Sigma Chemical Co. (St. Louis, Mo.). Cells were plated in 96-well microassay culture plates ($10^4$ cells/well) and grown overnight at 37° C. in a 5% $CO_2$ incubator. Drugs were then added to the wells to achieve a final drug concentration ranging from 0.1 to 50 μg/mL. Four wells were used for each concentration. Control wells were prepared by adding appropriate volumes of calcium- and magnesium-free PBS (pH 7.4). Wells containing culture medium without cells were used as blanks. The plates were incubated at 37° C. in a 5% $CO_2$ incubator for 72 hours. Upon completion of the incubation, 20 μL of stock MTT dye solution (5 mg/mL) was added to each well. After a 4-hour incubation, 100 μL of buffer containing 50% N,N-dimethylformamide and 20% SDS was added to solubilize the MTT formazan. Complete solubilization was achieved by placing the plate in a mechanical shaker for 30 minutes at room temperature. The optical density of each well was then measured with a microplate spectrophotometer at a wavelength of 570 nm. The percent cell viability was calculated by the following equation:

% cell viability=(OD treated wells/OD control wells)×100 where OD is the mean optical density from four determinations. The percent cell viability values were plotted against the drug concentrations used, and the $ID_{50}$ was calculated from the curve. Cytotoxicity experiments were repeated at least three times.

Results and Discussion

Drug resistance, both de novo and acquired, by human tumors is currently a major factor limiting the effectiveness of chemotherapy. Thus, for the in vitro evaluation of substituted anthracyclines having C-3' alkylated anthracyclines modified at benzyl ring and having 4'-substituted-benzylated anthracyclines, the inventors selected two sensitive cell lines: a human carcinoma KB and MCF-7 human breast cancer, the multi-drug-resistant (MDR) counterpart of KB (KBV1 carcinoma), which overexpresses MDR1 gene that encodes a membrane transport glycoprotein (P-gp), the MCF-7NVP-16 cell line that overexpresses the multi-drug-resistant associated protein (MRP), and the MCF-7/dox cell line which overexpresses MDR1 gene. Using this system, the inventors evaluate a drug's cytotoxic potential against human tumors and at the same time identify compounds that might have unique activity against MDR tumors (Priebe et al, 1993).

Table 2 shows the in vitro evaluation of cytotoxic properties of WP791, WP790, WP786, WP785, WP784, WP778, WP775, WP774, WP758, WP757, WP756, WP755 and doxorubicin (DOX) in KB and KB-V1 cells.

TABLE 2

In Vitro Cytotoxicity against Sensitive And MDR Tumor Cell Lines[1]

| Compound | KB μg/ml | KB-V1 μg/ml | RI[2] |
|---|---|---|---|
| WP786 | 0.60 ± 0.20 | 4.9 ± 0.2 | 8.1 |
| WP784 | 2.9 ± 0.8 | 0.8 Only one test | — |
| WP785 | 0.43 ± 0.05 | 49 ± 12 | 114 |
| WP790 | 3.93 ± 0.81 | 4.6 ± 2.3 | 1.2 |
| WP791 | 0.67 ± 0.25 | 4.6 ± 3.2 | 7 |
| WP774 | 4.5 ± 1.3 | 6.3 3.5 | 1.4 |
| WP775 | 0.4 ± 0.2 | 4.1 ± 3.5 | 10 |
| DOX | 0.50 ± 0.0 | >100 | >200 |
| WP755 | 1.50 ± 0.80 | 1.80 ± 0.80 | 1.20 |
| WP756 | 2.60 ± 0.30 | 2.80 ± 0.30 | 1.08 |
| WP757 | 0.67 ± 0.15 | 24.00 | 36 |
| WP758 | 0.67 ± 0.06 | 2.77 ± 0.25 | 4.13 |
| WP778 | 0.67 ± 0.41 | 3.83 ± 2.75 | 5.7 |
| DOX | 0.43 ± 0.19 | 109 ± 28 | 253 |

[1]mean of at least 4 experiments; MTT assay

Table 3 shows in vitro cytotoxic properties of WP783, WP750, WP744 and doxorubicin (DOX) in KB, KB-V1, MCF-7 and MCF-7/VP-16 cells

TABLE 3

In Vitro Cytotoxicity against Sensitive and Typical MDR and MRP Tumor Cell Lines[1]

| | KB | KBV1 | RI[2] | MCF-7 | MCF-7/VP-16 | RI[3] | MCF-7/DOX | RI[4] |
|---|---|---|---|---|---|---|---|---|
| EXP. 1 | | | | | | | | |
| WP744 | 1.44 ± 0.45 | 2.76 ± 0.52 | 1.84 | 1.63 ± 0.5 | 2.3 ± 1.9 | 1.41 | 5.25 | 3.22 |
| DOX | 2.35 | >100 | >42.6 | 0.3 | 3.0 | 10 | >100 | >333 |
| EXP. 2 | | | | | | | | |
| WP744 | 1.4 ± 0.45 | 2.1 ± 0.5 | 1.5 | 1.6 ± 0.5 | 2.3 ± 0.9 | 1.4 | | |
| DOX | 2.1 ± 0.8 | 174 ± 32 | 82.9 | 0.50 ± 0.26 | 8.3 ± 0.5 | 16.6 | | |
| WP744 | 0.48 ± 0.03 | 4.07 ± 1.85 | 8.5 | 0.37 ± 0.11 | 0.60 ± 0.10 | 1.6 | 0.89 ± 0.10 | 2.41 |
| DOX | 0.60 ± 0.13 | >100 | >167 | 0.53 ± 0.25 | 6.87 ± 0.58 | 13 | >100 | >189 |
| WP783 | 0.43 ± 0.21 | 1.1 ± 0.8 | 2.6 | | | | | |
| WP750 | 6.4 | 56 ± 29 | 8.8 | | | | | |
| DOX | 0.50 ± 0.0 | >100 | >200 | | | | | |

Table 4 shows data for fragmented DNA expressed as percentage of total DNA determined by quantitative apoptotic fragmentation assay in CEM leukemic cells incubated with drugs for 24 h. Results are from two independent studies carried out in duplicate.

TABLE 4

Apoptotic Fragmentation by WP744 in Comparison to Doxorubicin.

| Concentration | WP744 | | DOX | |
|---|---|---|---|---|
| μM | % Total DNA | SE | % Total DNA | SE |
| 0 | 0 | | 0 | |
| 0.05 | 17.8 | 6.8 | | |
| 0.1 | 31.3 | 12.9 | −0.2 | 0.3 |
| 0.5 | 46.7 | 9.8 | 27.1 | 12.7 |
| 1 | | | 28.7 | 9 |
| 2 | | | 38.3 | 7.4 |

Direct comparisons of the cytotoxicity of WP791, WP790, WP786, WP785, WP784, WP783, WP778, WP775, WP774, WP758, WP757, WP756, WP755, WP750 with DOX indicated that the C-3' and C-4' substitutions drastically increase the potency of those compounds. Compound WP785 displayed similar profile of activity to doxorubicin and its RI was of 114 was clearly higher than that of other analogs tested.

EXAMPLE 5

Treatment of Tumors with Analogs of Anthracyclines with Substitutions at C-3' or C-4' Sugars Treatment with the substituted anthracyclines having C-3'-alkylated anthracyclines modified at benzyl ring or having C-4'-substituted-benzylated anthracyclines of the present invention is similar to the treatment regimes of other anthracyclines and their derivatives, although some modifications to dosage may be warranted For example, standard treatment with doxorubicin is described in *Remington's Pharmaceutical Sciences* as follows.

Doxorubicin is administered intravenously to adults at 60 to 75 mg/m² at 21-day intervals or 25 to 30 mg/m² on each of 2 or 3 successive days repeated at 3- or 4-week intervals or 20 mg/m² once a week. The lowest dose should be used in elderly patients, when there is prior chemotherapy or neoplastic marrow invasion or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m² in patients with normal heart function and 400 mg/m² in patients with abnormal heart function and 400 mg/m² on each of 3 consecutive days, repeated every 4 weeks. Prescribing limits are as with adults. It has been reported that a 96-hour continuous infusion is as effective as and much less toxic than the same dose given by golus injections.

Of course, modifications of the treatment regimes due to the unique nature of the substituted anthracyclines having C-3'-alkylated anthracyclines modified at benzyl ring and having C-4'-substituted anthracyclines of the present invention are possible and well within the ability of one skilled in the art. Appropriate modifications may be ascertained by following the protocols in the following examples for in vivo testing and developments of human protocols.

EXAMPLE 6

In Vivo Prevention of Tumor Development using Analogs of Anthracyclines with Substitutions at C-3' or C-4' Sugars In an initial round of in vivo trials, a mouse model of human cancer with the histologic features and metastatic potential resembling tumors seen in humans (Katsumata et al., 1995) is used. The animals are treated with analogs of anthracyclines having C-3'-substitutions as described or anthracycline analogs with C-4'-substitutions synthesized in the present invention to determine the suppression of tumor development.

These novel analogs are tested in vivo for anti-tumor activity against murine leukemia L1210, P388, and P388 resistant to doxorubicin. In conjunction with these studies, the acute and sub-acute toxicity is studied in mice (LD10, LD50, LD90). In a more advanced phase of testing, the anti-tumor activity of substituted anthracyclines synthesized in the present invention, are tested against human xenografts is assessed and cardiotoxicity studies performed is done in a rat or rabbit model.

These studies are based on the discovery that these analogs of anthracyclines have anti-cancer activity for MDR cancer cells. The invention provides a useful preventive and therapeutic regimen for patients with MDR tumors.

Two groups of mice of a suitable cancer model are treated with doses of substituted anthracyclines with substitutions at the C-3'-sugar or having C-4'-substituted sugar moietied. Several combinations and concentrations of the substituted anthracyclines are tested. Control mice are treated with buffer only.

The effect of substituted anthracyclines on the development of breast tumors is compared with the control group by examination of tumor size and histopathologic examination (breast tissue is cut and stained with hematoxylin and eosin) of breast tissue. With the chemopreventive potential of WP831, WP791, WP790, WP787, WP786, WP785, WP784, WP780, WP778, WP775, WP774, WP758, WP757, WP756, WP755, WP799, WP797, WP794, WP783, WP750, WP744, WP727, WP571, WP418 and WP417, it is predicted that, unlike the control group of mice that develop tumors, the testing group of mice is resistant to tumor development.

EXAMPLE 7

Human Treatment with Analogs of Anthracyclines with Substitutions at C-3' or C-4' Sugars This example describes a protocol to facilitate the treatment of cancer using substituted anthracyclines having C-3' alkylated anthracyclines modified at benzyl ring and having 4'-substituted-benzylated anthracyclines.

A cancer patient presenting, for example, an MDR cancer is treated using the following protocol. Patients may, but need not, have received previous chemo- radio- or gene therapeutic treatments. Optimally, the patient exhibits adequate bone marrow function (defined as peripheral absolute granulocyte count of >2,000/mm3 and platelet count of 100,000/mm3, adequate liver function (bilirubin 1.5 mg/dl) and adequate renal function (creatinine 1.5 mg/dl)).

Exemplary Protocol for the Treatment of Multi-Drug Resistant Cancer

A composition of the present invention is typically administered orally or parenterally in dosage unit formulations containing standard, well known, non-toxic physiologically acceptable carriers, adjuvants, and vehicles as desired. The term parenteral as used herein includes subcutaneous injections, intravenous, intramuscular, intra-arterial injection, or infusion techniques. The analogs of anthracyclines synthesized in the present invention may be delivered to the patient before, after, or concurrently with the other anti-cancer agents.

A typical treatment course may comprise about six doses delivered over a 7- to 21-day period. Upon election by the clinician, the regimen may be continued six doses every three weeks or on a less frequent (monthly, bimonthly, quarterly etc.) basis. Of course, these are only exemplary times for treatment, and the skilled practitioner will readily recognize that many other time-courses are possible.

A major challenge in clinical oncology is that many cancers are multi-drug resistant. One goal of the inventors' efforts has been to find ways to improve the efficacy of chemotherapy. In the context of the present invention, the substituted anthracyclines have a surprising cytotoxicity against such cancers.

To kill MDR cancer cells using the methods and compositions described in the present invention, one will generally contact a target cell with a bisanthracycline of the present invention. These compositions are provided in an amount effective to kill or inhibit the proliferation of the cell.

In certain embodiments, it is contemplated that one would contact the cell with agent(s) of the present invention about every 6 hours to about every one week. In some situations, however, it may be desirable to extend the time period for treatment significantly where several days (2, 3, 4, 5, 6, 7 or more) to several weeks (1, 2, 3, 4, 5, 6, 7, or more) lapse between respective administrations.

Regional delivery of anthracycline analogs is an efficient method for delivering a therapeutically effective dose to counteract the clinical disease. Likewise, the chemotherapy may be directed to a particular affected region. Alternatively, systemic delivery of active agents may be appropriate.

The therapeutic composition of the present invention is administered to the patient directly at the site of the tumor. This is in essence a topical treatment of the surface of the cancer. The volume of the composition should usually be sufficient to ensure that the tumor is contacted by the substituted anthracyclines.

In one embodiment, administration simply entails injection of the therapeutic composition into the tumor. In another embodiment, a catheter is inserted into the site of the tumor, and the cavity may be continuously perfused for a desired period of time.

Clinical responses may be defined by acceptable measure. For example, a complete response may be defined by the disappearance of all measurable disease for at least a month, whereas a partial response may be defined by a 50% or greater reduction of the sum of the products of perpendicular diameters of all evaluable tumor nodules or at least one month with no tumor sites showing enlargement. Similarly, a mixed response may be defined by a reduction of the product of perpendicular. diameters of all measurable lesions by 50% or greater, with progression in one or more sites.

Of course, the above-described treatment regimes may be altered in accordance with the knowledge gained from clinical trials such as those described in Example 7. Those of skill in the art are able to take the information disclosed in this specification and optimize treatment regimes based on the clinical trials described in the specification.

EXAMPLE 8

Clinical Trials with Analogs of Anthracyclines with Substitutions at C-3' or C-4' on the Sugar Moiety This example is concerned with the development of human treatment protocols using the substituted anthracyclines. These compounds are of use in the clinical treatment of various MDR cancers in which transformed or cancerous cells play a role. Such treatment is a particularly useful tool in anti-tumor therapy, for example, in treating patients with ovarian, breast and lung cancers that are resistant to conventional chemotherapeutic regimens.

The various elements of conducting a clinical trial, including patient treatment and monitoring, is known to those of skill in the art in light of the present disclosure. The following information is being presented as a general guideline for use in establishing substituted anthracyclines drugs made by the use of this invention, in clinical trials.

Patients with human metastatic breast and/or epithelial ovarian carcinoma, colon cancer leukemia, or sarcoma are chosen for clinical study. Measurable disease is not required, however the patient must have easily accessible pleural effusion and/or ascites. Further the patients must carry tumors that express MDR phenotype. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile.

In regard to the substituted anthracyclines drug administration, a Tenckhoff catheter, or alternative device, may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15-3, CA 125, p185) and in the cells (E1A, p185) may be assessed and recorded.

In the same procedure, substituted anthracyclines may be administered. The administration may be in the pleural/peritoneal cavity, directly into the tumor, or in a systemic manner. The starting dose may be 0.5 mg/kg body weight. Three patients may be treated at each dose level in the absence of grade >3 toxicity. Dose escalation may be done by 100% increments (0.5 mg, 1 mg, 2 mg, 4 mg) until drug related Grade II toxicity is detected. Thereafter, dose escalation may proceed by 25% increments. The administered dose may be fractionated equally into two infusions, separated by 6 hours if the combined endotoxin levels determined for the lot of bisanthracycline exceed 5EU/kg for any given patient The substituted anthracyclines may be administered over a short infusion time or at a steady rate of infusion over a 7- to 21-day period. The bisanthracycline infusion may be administered alone or in combination with the anti-cancer drug. The infusion given at any dose level is dependent upon the toxicity achieved after each. Hence, if Grade II toxicity was reached after any single infusion, or at a particular period of time for a steady rate infusion, further doses should be withheld or the steady rate infusion stopped unless toxicity improves. Increasing doses of substituted anthracyclines in combination with an anti-cancer drug is administered to groups of patients until approximately 60% of patients show unacceptable Grade III or IV toxicity in any category. Doses that are ⅔ of this value could be defined as the safe dose.

Physical examination, tumor measurements, and laboratory tests should, of course, be performed before treatment and at intervals of about 3–4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum should be monitored, e.g. CEA, CA 15–3, p185 for breast cancer, and CA 125, p185 for ovarian cancer.

To monitor disease course and evaluate the anti-tumor responses, it is contemplated that the patients should be examined for appropriate tumor markers every 4 weeks, if initially abnormal, with twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytoperia Coagulation profile shall be obtained every 4 weeks. An SMA-12-100 shall be performed weekly. Pleural/peritoneal effusion may be sampled 72 hours after the first dose, weekly thereafter for the first two courses, then every 4 weeks until progression or off study. Cellularity, cytology, LDH, and appropriate markers in the fluid (CEA, CA15–3, CA 125, p185) and in the cells (p185) may be assessed. For an example of an evaluation profile, see Table 3. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. A urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least one month with no tumor sites showing enlargement. Similarly, a mixed response may be defined by a reduction of the product of perpendicular diameters of all measurable lesions by 50% or greater with progression in one or more sites.

TABLE 5

EVALUATIONS BEFORE AND DURING THERAPY

| EVALU-ATIONS | PRE-STUDY | TWICE WEEKLY | WEEKLY | EVERY 4 WEEKS | EVERY 8 WEEKS |
|---|---|---|---|---|---|
| History | X | | | X | |
| Physical | X | | | X | |
| Tumor Measurements | X | | | X | |
| CBC | X | $X^1$ | X | | |
| Differential | X | $X^1$ | X | | |
| Platelet Count | X | $X^1$ | X | | |
| SMA12-100 (SGPT, Alkaline Phosphatase, Bilirubin, A1b/ Total Protein) | X | | X | | |
| Coagulation Profile | X | | | X | |
| Serum Tumor markers (CEA, CA15-3, CA-125, Her-2/neu) | X | | | | $X^3$ |
| Urinalysis | X | | | X | |
| X-rays: | | | | | |
| chest | X | | $X^4$ | | |
| others | X | | | | X |
| Pleural/Peritoneal Fluids: (cellularity, cytology, LDH, tumor markers, E1A, HER-2/neu) | X | | $X^5$ | X | |
| Spirometry and DLCO | X | | | $X^6$ | $X^6$ |

$^1$For the first 4 weeks, then weekly, if no myelosuppression is observed.
$^2$As indicated by the patient's condition.
$^3$Repeated every 4 weeks if initially abnormal.
$^4$For patients with pleural effusion, chest X-rays may be performed at 72 hours after first dose, then prior to each treatment administration.
$^5$Fluids may be assessed 72 hours after the first dose, weekly for the first two courses and then every 4 weeks thereafter.
$^6$Four and eight weeks after initiation of therapy.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Arcamone F., *Doxorubicin*. Anti-Cancer Antibiotics. New York: Academic Press, 1981.
Bell et al., *J. Clin. Oncol.*, 3:311, 1985
Bertino, *J. Clin. Oncol.*, 3:293, 1985
Bodley, et al., *Cancer Res.*, 49:5969–5978, 1989.
Bodley et al., *Cancer Res.*, 49:5969.
Booser D J and Hortobagyi G N., "Anthracycline Antibiotics in Cancer Therapy. Focus on Drug Resistance", *Drugs*, 47:223–258, 1994.
Bradley et al., *Biochem. Biophys. Acta.*, 948:87, 1988.
Capranico et al., "Sequence-Selective Topoisomerase II Inhibition by Anthracycline Derivatives in SV40 DNA: Relationship with DNA Binding Affinity and Cytotoxicity", *Biochem*, 29:562–569, 1990.
Curt et al., *Cancer Treat. Rep.*, 68:87, 1984.
Danks et al., *Cancer Res.*, 47:1297, 1987.
Denny et al., "Potential Anti-tumor Agents. 39. Anilino Ring Geometry of Amsacrine and Derivatives: Relationship to DNA binding and Anti-tumor Activity", *J. Med. Chem.*, 26(11):1625–1630, 1983.
Dervan P. *Science*, 232:464–471, 1986.
Fojo et al., *P.N.A.S.*, 84:265, 1987.
Ganapath, et al., *Br. J. Cancer*, 60:819, 1989.

Goldie et al., *Cancer Res.*, 44:3643, 1984.
Goldie et al., *Cancer Treat. Rep.*, 63:1127, 1979.
Green et al., *J. Immunol. Methods*, 70:257–268, 1984.
Gros et al., *Nature*, 323:728, 1986
Israel et al., 1987.
Israel et al., *Cancer Chemother. Pharmacol.*, 25:177, 1989.
Katswnata et al., "Prevention of Breast Tumor Development In Vivo by Down-Regulation of the p185$^{neu}$ Receptor", *Nature Med*, 1:644–648, 1995.
Kolate, *Science*, 231:220, 1986.
Lown J W, "Targeting the DNA Minor Groove for Control of Biological Function: Progress, Challenges and Prospects", *Chemtracts—Org. Chem.*, 6:205–237, 1903.
Lown J W, "*Anthracycline and Anthracenedione-Based Anticancer Agents*. Bioactive Molecules, Vol. 6, Amsterdam: Elsevier, 1988.
Norris et al., "Expression of the gene for multi-drug-resistance-associated protein and outcome in patients with neuroblastoma", *N. Engl. J. Med.* 334:231–238, 1996.
Nowell, *Cancer Res.*, 46:2203, 1986.
Pommier et al., *Cancer Res.*
Priebe et al., "3'-Hydroxy-esorubicin substituted at C-2'", *J. Antibiot*, 45:386–393, 1992.
Priebe et al., "Removal of the basic center from doxorubicin partially overcomes multi-drug resistance and decreases cardiotoxicity", *Anti-Cancer Drugs*, 4:37–48, 1993.
Priebe W, "Anthracycline Antibiotics. Novel Analogues, Methods of Delivery, and Mechanisms of Action", Washington, DC: American Chemical Society, 1995.
Priebe W. "Mechanism of Action-Governed Design of Anthracycline Antibiotics: A "Turn-Off/Turn-On" Approach", *Current Pharmaceutical Design*, 1:51–68, 1995.
Rubinstein et al., "Comparison of In Vitro Anti-Cancer-Drug-Screening Data Generated with A Tetazolium Assay Versus a Protein Assay Against a Diverse Panel of Human Tumor Cell Lines", *J. Nat'l. Cancer Inst.*, 82:1113–1120, 1990.
Stryer, "Biochemistry", Freeman and Co., 1981.
Sweatman et al, *J. Cell. Pharmacol.*, 1:95–102.
Traganos et al., *Cancer Res.*, 45:6273, 1985.
Wakelin L P G, "Medicinal Research Rev.", 6:275–340, 1986.
Young et al., *N. Engl. J. Med*, 312:692, 1985.
U.S. Pat. No. 4,263,428 Apr. 21, 1981.
U.S. Pat. No. 4,345,070, Aug. 17, 1982.
U.S. Pat. No. 4,438,105, Mar. 20, 1984.

The invention claimed is:
1. A substituted anthracycline of the formula:

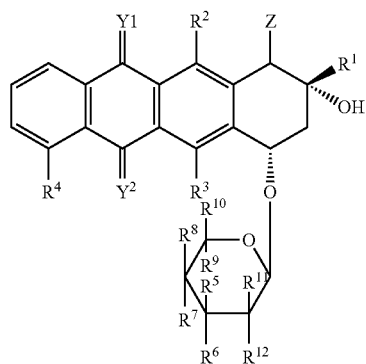

wherein, $R^1$ is an alkyl chain, a (—COCH$_2$R$^{13}$) group, or a (C(OH)—CH$_2$R$^{13}$) group;

wherein, $R^{13}$ is a hydrogen (—H) group, a hydroxyl group (—OH), a methoxy group (—OCH$_3$), an alkoxy group comprising 1–20 carbon atoms, an alkyl group comprising 1–20 carbon atoms, an aryl group comprising 1–20 carbon atoms, a fatty acyl group comprising the general structure —O—CO(CH$_2$)$_n$CH$_3$, wherein n=an integer from 1 to about 20, a fatty acyl group comprising the general structure —O—CO(CH$_2$)$_l$(CH=CH)$_m$(CH$_2$)$_n$CH$_3$, wherein l is an integer between 1 to 3, m is an integer between 1 and 6, and n is an integer between 1 and 9, a —OCO—(CH$_2$)$_n$—CH$_2$NH$_2$, group, or a —OCO—(CH$_2$)$_n$—CO$_2$H group;

wherein $R^2$ and $R^3$ are, independently of the other, a hydrogen (—H), a hydroxyl group (—OH), or a methoxy group (—OCH$_3$);

$R^4$ is a hydrogen (—H) group, a methoxy group (—OCH$_3$), a hydroxyl group (—OH), or a halide;

wherein $Y^1$ and $Y^2$ are, independently of the other, a double bonded oxygen, sulphur, or nitrogen atom;

wherein Z is a —H, —OH, a —CO$_2$H, or a —CO$_2$R group;

wherein $R^7$, $R^8$, are, independently, —H, —OH, a halide, —OR$^{19}$, —SH, —SR$^{19}$, —NH$_2$, —NHR$^{19}$, —N(R$^{19}$)$_2$, or —CH$_3$, and $R^7$ can additionally be a saccharide, wherein $R^{19}$ is an alkyl chain, an alkylating moiety, a cycloalkyl chain, a cyclic ring, or a hydrogen;

wherein $R^9$ is an —H, —CH$_3$, alkyl, aryl, CH$_2$OH, or, a CH$_2$F group;

wherein $R^{10}$, $R^{11}$ and $R^{12}$ are, independently, —H, —OH, a halide, —OR, —SH, —SR, —NH$_2$, —NHR, —N(R)$_2$, or a —CH$_3$;

wherein one of $R^5$ and $R^6$ is an —H;

wherein one of $R^5$ and $R^6$ is a X-alkyl-aromatic-ring (—XAAR) substituent wherein, A is an alkyl group and wherein, AR is an substituted phenyl ring, a substituted five-member ring, a heteroatomic five-member ring, or a heteroatomic six-member ring, of the form:

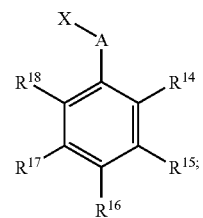

wherein at least one of $R^{14}$–$R^{18}$ is an a (—H) group and wherein at least one of $R^{14}$–$R^{18}$ is a hydroxyl group (—OH), a methoxy group (—OCH$_3$), a nitro group (—NO$_2$), an amine group (—NH$_2$), a halide, an alkoxy group comprising 1–20 carbon atoms, an alkyl group comprising 1–20 carbon atoms, an aryl group comprising 1–20 carbon atoms, an alkyl-amino group, an alkyl-thio group, a cyano group (CN, SCN), a —CO$_2$H group, or a —CO$_2$R group; and X is a —O, —N, —S, —SO, or a —SO$_2$ group; and A is (CH$_2$)$_n$ where n=0–10;

wherein, if $R^5$ is a XAAR substituent $R^6$ is not and if $R^6$ is a XAAR substituent $R^5$ is not.

2. A substituted anthracycline of the formula:

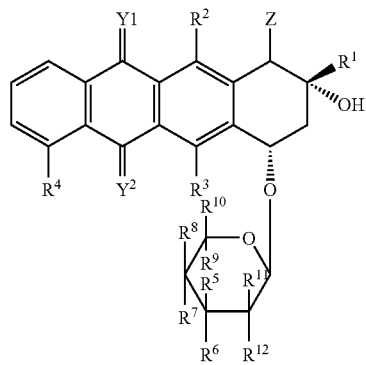

wherein, $R^1$ is an alkyl chain, a (—$COCH_2R^{13}$) group, or a (C(OH)—$CH_2R^{13}$) group;

wherein, $R^{13}$ is a hydrogen (—H) groups a hydroxyl group (—OH), a methoxy group (—$OCH_3$), an alkoxy group comprising 1–20 carbon atoms, an alkyl group comprising 1–20 carbon atoms, an aryl group comprising 1–20 carbon atoms, a fatty acyl group comprising the general structure —O—CO($CH_2$)$_n$$CH_3$, wherein n=an integer from 1 to about 20, a fatty acyl group comprising the general structure —O—CO($CH_2$)$_l$(CH=CH)$_m$($CH_2$)$_n$$CH_3$, wherein l is an integer between 1 to 3, m is an integer between 1 and 6, and n is an integer between 1 and 9, a —OCO—($CH_2$)$_n$—$CH_2NH_2$ group or a —OCO—($CH_2$)$_n$—$CO_2H$ group;

wherein $R^2$ and $R^3$ are, independently of the other, a hydrogen (—H), a hydroxyl group (—OH), or a methoxy group (—$OCH_3$);

wherein $R^4$ is a hydrogen (—H) group, a methoxy group (—$OCH_3$), a hydroxyl group (—OH), or a halide;

wherein $Y^1$ and $Y^2$ are, independently of the other, a double bonded oxygen, sulphur, or nitrogen atom;

wherein Z is a —H, —OH, a —$CO_2H$, or a —$CO_2R$ group;

wherein $R^5$ and $R^6$, are, independently, —H, —OH, a halide, —$OR^{19}$, —SH, —$SR^{19}$, —$NH_2$, —$NHR^{19}$, —$N(R^{19})_2$ or —$CH_3$, and $R^5$ can additionally be an alkylating moiety, wherein $R^{19}$ is an alkyl chain, an alkylating moiety, a cycloalkyl chain, a cyclic ring, a hydrogen;

wherein $R^9$ is an —H, —$CH_3$, alkyl, aryl, $CH_2OH$, or $CH_2F$ group;

wherein $R^{10}$, $R^{11}$, and $R^{12}$ are, independently, —H, —OH, a halide, —OR, —SH, —SR, —$NH_2$, —NHR, —$N(R)_2$ or —$CH_3$;

wherein one of $R^7$ and $R^8$ is an —H and wherein one of $R^7$ and $R^8$ is a X-alkyl aromatic-ring (—XAAR) substituent, wherein, A is an alkyl group and wherein, AR is an unsubstituted phenyl ring, a substituted phenyl ring, a substituted five-member ring or a heteroatomic five-member ring, of the general form;

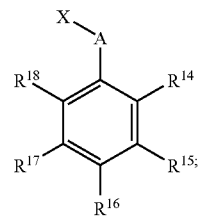

wherein, $R^{14}$–$R^{18}$ are independently a (—H) group, a hydroxyl group (—OH), a methoxy group (—$OCH_3$), a nitro group (—$NO_2$), an amine group (—$NH_2$), a halide, an alkoxy group having 1–20 carbon atoms, an alkyl group having 1–20 carbon atoms, an aryl group having 1–20 carbon atoms, an alkyl-amino group, an alkyl-thio group, a cyano group (CN, SCN), an —$CO_2H$ group, or a —$CO_2R$ group; and X is a —O, —N, —S, —SO, or a —$SO_2$ group; and A is ($CH_2$)$_n$, where n=0–10;

wherein if $R^7$ is a XAAR substituent $R^8$ is not and if $R^8$ is a XAAR substituent $R^7$ is not.

3. The substituted anthracycline of claim 1, wherein the aromatic ring of the —XAAR substituent is disubstituted, trisubstituted, tetrasubstituted, or pentasubstituted.

4. The substituted anthracycline of claim 1, wherein the substituted anthracycline is formulated into a pharmaceutically acceptable carrier.

5. The substituted anthracycline of claim 2, wherein the aromatic ring of the —XAAR substituent is disubstituted, trisubstituted, tetrasubstituted, or pentasubstituted.

6. The substituted anthracycline of claim 2, wherein the substituted anthracycline is formulated into a pharmaceutically acceptable carrier.

7. A method of treating or preventing cancer comprising administering to a patient a substituted anthracycline of claim 1 or claim 2.

8. The method of claim 7, wherein the substituted anthracycline is formulated into a pharmaceutically acceptable carrier.

9. The method of claim 7, wherein the substituted anthracycline is the substituted anthracycline of claim 1.

10. The method of claim 7, wherein the substituted anthracycline is the substituted anthracycline of claim 2.

11. The method of claim 7, wherein the cancer is breast cancer, lung cancer, ovarian cancer, Hodgkin's disease, non-Hodgkin's lymphoma, acute leukemia, or carcinoma of the testes.

12. The method of claim 11, wherein the cancer is breast cancer.

13. The substituted anthracycline of claim 1 of the formula:

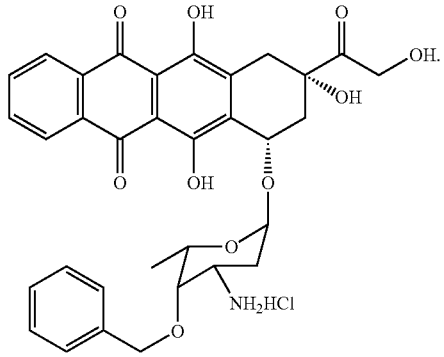

* * * * *

UNITED STATES PATENT AND TRADEMARK OFFICE
CERTIFICATE OF CORRECTION

PATENT NO. : 7,109,177 B2
APPLICATION NO. : 10/752426
DATED : September 19, 2006
INVENTOR(S) : Priebe et al.

Page 1 of 1

It is certified that error appears in the above-identified patent and that said Letters Patent is hereby corrected as shown below:

Title page, item [75], line 1, delete "Waldeman" and insert --Waldemar-- therefor.

In claim 2, column 43, line 19, delete "groups" and insert --group, -- therefor.

In claim 2, column 43, line 43, after "ring", insert -- or --therefor.

Signed and Sealed this

Twenty-third Day of January, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,109,177 B2 | Page 1 of 1 |
| APPLICATION NO. | : 10/752426 | |
| DATED | : September 19, 2006 | |
| INVENTOR(S) | : Waldemar Priebe et al. | |

It is certified that error appears in the above-identified patent and that said Letters Patent is hereby corrected as shown below:

In column 1, lines 13-15, delete "The U.S. Government may owns rights in the present invention pursuant to National Institute of Health grants numbered C3A55270 and CA50320." and insert --This invention was made with government support under grants numbered C3A55270 and CA50320 awarded by the National Institutes of Health. The government has certain rights in the invention.-- therefor.

Signed and Sealed this

Sixteenth Day of October, 2007

JON W. DUDAS
*Director of the United States Patent and Trademark Office*